US005703213A

United States Patent [19]
Wands et al.

[11] Patent Number: 5,703,213
[45] Date of Patent: Dec. 30, 1997

[54] MONOCLONAL ANTIBODIES WHICH RECOGNIZE AN ADENOCARCINOMA CELL ANTIGEN

[75] Inventors: Jack R. Wands, Wabun, Mass.; Hiroshi Takahashi, Tokyo, Japan

[73] Assignee: The General Hospital Corporation, Boston, Mass.

[21] Appl. No.: 193,673

[22] Filed: Feb. 7, 1994

Related U.S. Application Data

[63] Continuation of Ser. No. 31,873, Mar. 16, 1993, abandoned, which is a continuation of Ser. No. 857,716, Mar. 25, 1992, abandoned, which is a continuation of Ser. No. 203,182, Jun. 7, 1988, abandoned, which is a continuation-in-part of Ser. No. 130,777, Dec. 9, 1987, abandoned, and Ser. No. 180,913, Apr. 13, 1988, abandoned.

[51] Int. Cl.$^6$ .............. C12N 5/20; C12N 5/12; C12N 5/18; C07K 16/30; C12P 21/08
[52] U.S. Cl. .............. 530/388.85; 530/387.7; 530/388.8; 435/240.27; 435/172.2; 435/70.21
[58] Field of Search .............. 530/387.7, 388.8, 530/388.85; 435/240.27, 72.2, 70.21

[56] References Cited

U.S. PATENT DOCUMENTS

| | | |
|---|---|---|
| 4,349,528 | 9/1982 | Koprowski . |
| 4,444,744 | 4/1984 | Goldenberg . |
| 4,485,093 | 11/1984 | Runge . |
| 4,536,479 | 8/1985 | Vander-Mallie . |
| 4,571,382 | 2/1986 | Adachi . |
| 4,661,586 | 4/1987 | Levy et al. . |
| 4,683,200 | 7/1987 | Hirohashi et al. . |
| 4,695,538 | 9/1987 | Cote et al. . |
| 4,877,611 | 10/1989 | Cantrell .............. 424/277.1 |
| 5,212,085 | 5/1993 | Wands et al. .............. 435/240.27 |

FOREIGN PATENT DOCUMENTS

0119556A2  9/1984  European Pat. Off. .

OTHER PUBLICATIONS

Goding, J.W., *Monoclonal Antibodies: Principles and Practice*, Academic Press, Inc., Orlando, Florida, pp. 118–125 (1983).
Takahashi, H. et al., *Cancer Res.* 48:6573–6579 (1988).
Wilson, B.E. et al., *Hepatology* 7(5): Abstract No. 416 (1987).
Wilson, B. et al., *Proc. Natl. Acad. Sci. USA*. 85: 3140–3144 (1988).
Lloyd, in: Herberman, ed., *Basic and Clinical Tumor Immunology* 1:159–214 (1983).
Davis, et al., In: Prasad et al., eds., *Novel Approaches to Cancer Chemotherapy*, Academic Press, New York (1984), p. 43.
Gatter et al., *Semin. Oncol.* IX:517–525 (1982).
Neville et al., *Hum. Pathol.* 13:1067–1081 (1982).
Levy et al., *Ann. Rev. Med.* 34:107–110 (1983).
Herlyn et al., *Proc. Natl. Acad. Sci. USA* 76:1438–1442 (1979).
D. M. Herlyn et al., *Canc. Res.* 40:717 (1980).
Chang et al., *Hybridoma* 1:37 (1981).
Steplewski et al., *Canc. Res.* 41:2723 (1982).
D.M. Herlyn et al., *Int. J. Canc.* 27:769 (1981).
D. Herlyn et al., *Proc. Nat. Acad. Sci. U.S.A.* 79:4761 (1982).
Atkinson et al., *Canc. Res.* 42:4820 (1982).
Magnani et al., *Science* 212:55 (1981).
Magnani et al., *J. Biol Chem.* 257:14365 (1982).
Magnani, J.L., et al., *Canc. Res.* 43:5489–5492 (1983).
Sears et al., *Lancet* ii 762 (1982).
Finan et al., *Br. J. Cancer* 46:9 (1982).
Thompson et al., *Br. J. Cancer* 47:595 (1983).
Lindholm et al., *Intl. Arch. Allergy Appl. Immunol.* 71: 178 (1983).
Stramignoni et al., *Int. J. Cancer* 31:543 (1983).
Shen et al., *Int. J. Cancer* 33:465 (1984).
Kaszubowski et al., *Canc. Res.* 44:1194 (1984).
Koprowski et al., *Proc. Natl. Acad. Sci. USA* 81:216 (1984).
Herlyn, M., et al., *J. Immunol. Meth.* 80:107–116 (1985).
Sakamoto et al., *Fed. Proc.* 44:792 (1985).
Shi et al., *Canc. Res.* 44:1142 (1984).
Fukushima et al., *Canc. Res.* 44:55279 (1984).
Lan et al., *Canc. Res.* 45:305 (1985).
Drewinko et al., *Canc. Res.* 46:5137 (1986).
Hand et al., *Canc. Res.* 45:833 (1985).
Johnson et al., *Canc. Res.* 46:850 (1986).
Paterson et al., *Int. J. Cancer* 37:659 (1986).
Muraro et al., *Int. J. Cancer* 39:34 (1987).
Bleday et al., *Cancer* 57:433 (1986).
Wands et al., *Gastroenterol.* 80:225 (1981).
Carlin et al., *Exp. Cell Res.* 147:359 (1983).
Moriarty et al., *Hybridoma* 2:39 (1983).
He et al., *In Vitro* 20:493 (1984).
Carlson et al., *J. Clin. Invest.* 76:40 (1985).
Shouval et al., *Hepatology* 5:347 (1985).
Hu et al., *Hepatology* 6:1396 (1986).
Wiedmann et al., *Hepatology* 7:543 (1987).
Anderson et al., *Science* 220:542 (1983).
Macklis et al., *Brain Res.* 359:158 (1985).
Mew et al., *Canc. Res.* 45:4380 (1985).
Oseroff et al., *Proc. Natl. Acad. Sci. USA* 83:8744 (1986).
Oseroff et al., *Photochem. Photobiol.* 46:83 (1987).
Esteban et al., *J. Nucl. Med.* 28:861 (1987).
Hobbs et al., *J. Dermatol. Surg. Oncol.* 13:955 (1986).
Manyak et al., *J. Clin. Oncol.* 6:380 (1988).

*Primary Examiner*—Anthony C. Caputa
*Attorney, Agent, or Firm*—Sterne, Kessler, Goldstein & Fox P.L.L.C.

[57] ABSTRACT

The present invention is directed to antibodies, and fragments thereof, which specifically bind the AF-20 and the XF-8 epitopes of adenocarcinoma cell antigen(s).

10 Claims, 9 Drawing Sheets

```
SKIN            •     FOCUS

MUSCLE          ●     HEPATOMA 1

LUNG                  NORMAL LIVER 1

STOMACH         ●     HEPATOMA 2

COLON                 NORMAL LIVER 2

LIVER           ●     HEPATOMA 3

PANCREAS              NORMAL LIVER 3

KIDNEY          ●     HEPATOMA 4

SPLEEN                NORMAL LIVER 4
```

FIG. 5

MUSCLE      •      FOCUS

LUNG      ●      HEPATOMA 1

LIVER      ●      HEPATOMA 2

PANCREAS           NORMAL LIVER 2

COLON      ●      HEPATOMA 3

KIDNEY           NORMAL LIVER 3

ADRENAL      ●      HEPATOMA 4

SPLEEN           NORMAL LIVER 4

FIG. 8

| | | | | |
|---|---|---|---|---|
| MUSCLE | ● LS 180 | MUSCLE | | ● LUNG CA 1 |
| LUNG | ➤ NORMAL COLON | LIVER | | NORMAL LUNG 1 |
| LIVER | ● COLON CA 11 | PANCREAS | | ● LUNG CA 4 |
| PANCREAS | ● 14 | KIDNEY | | ● NORMAL LUNG 4 |
| KIDNEY | ● 15 | ADRENAL | ● | ● LUNG CA 5 |
| ADRENAL ● | ● 13 | SPLEEN | | ● NORMAL LUNG 5 |
| SPLEEN | ● 19 | | | |

FIG. 9A                     FIG. 9B

MONOCLONAL ANTIBODIES WHICH RECOGNIZE AN ADENOCARCINOMA CELL ANTIGEN

CROSS REFERENCE TO RELATED APPLICATIONS

This application is a continuation of U.S. application Ser. No. 08/031,873, filed Mar. 16, 1993, abandoned, which is a continuation of U.S. application Ser. No. 07/857,716, filed Mar. 25, 1992, abandoned, which is a continuation of U.S. application Ser. No. 07/203,182, filed Jun. 7, 1988, abandoned, which is a continuation-in-part of U.S. application Ser. Nos. 07/130,777, filed Dec. 9, 1987 and 07/180,913, filed Apr. 13, 1988, both of which are abandoned.

FEDERAL GOVERNMENT'S RIGHTS IN THIS INVENTION

This invention was made with government support under CA35711 awarded by the National Cancer Institute of the National Institutes of Health. The government has certain rights in the invention.

BACKGROUND OF THE INVENTION

FIELD OF THE INVENTION

The present invention is directed toward antigens which are associated with carcinoma cells, and especially with hepatocarcinoma cells, and adenocarcinoma cells of the colon and lung. The invention is further directed toward antibodies, and in particular, monoclonal antibodies, which are reactive against such antigens. The invention is further directed toward continuous hybridoma cell lines capable of secreting such monoclonal antibodies, and to methods of using these antibodies.

BACKGROUND OF THE INVENTION

A. THE ROLE OF MONOCLONAL ANTIBODIES

The ability to generate monoclonal antibodies has enabled the identification of tumor-associated antigens. Monoclonal antibodies of relevant specificities can be valuable reagents not only for immunodiagnosis and immunotherapy, but also in the study of tumor cells in general. Examples of various neoplasms to which monoclonal antibodies have been generated include leukemia (Seon et al., *Proc. Natl. Acad. Sci., USA* 80:845 (1983); Aota et al., *Cancer Res.* 43:1093 (1983); Royston et al., *Transplan. Proc.* 13:761 (1981)); glioma (Bourdin et al., *Canc. Res.* 43:2796 (1983); Schnegg et al., *Canc. Res.* 41:1209 (1981)); melanoma (Dippold et al., *Proc. Natl. Acad. Sci., USA* 77:6114 (1980); Carrel et al., *Canc. Res.* 40:2523 (1980)); breast carcinoma (Colcher et al., *Proc. Natl. Acad. Sci., USA* 78:3199 (1981); Schlom et al., *Proc. Natl. Acad. Sci., USA* 77:6841 (1980)); lung carcinoma (Cuttitta et al., *Proc. Natl. Acad. Sci., USA* 78:4591 (1981)); cervical carcinoma (Handley et al., PCT Publication No. WO 83/04313 (1983)); bladder carcinoma (Masuko et al., *J. Natl. Cancer Instit.* 72:523 (1984); Messing et al., *J. Urol.* 132:167 (1984); Grossman, *J. Urol.* 130:610 (1983); Stramignoni et al., *Intl. J. Cancer* 31:543 (1983); Herlyn et al., *Proc. Natl. Acad. Sci., USA* 76:1438 (1979); Kasai et al., *J. Surg. Res.* 30:403–408 (1981)); and prostate carcinoma (Ware et al., *Canc. Res.* 42:1215 (1982); Starling et al., *Canc. Res.* 42:3714 (1982)). The detection and characterization of human tumor antigens using monoclonal antibodies has been reviewed by Lloyd, "Human Tumor Antigens: Detection and Characterization with Monoclonal Antibodies," In: Herberman, ed., *Basic and Clinical Tumor Immunology* 1:159–214, Nijoff, Boston (1983). Lloyd's review includes a discussion of the use of monoclonal antibodies to detect colorectal cancer. Lloyd, supra, at 181–182.

B. HEPATOCARCINOMA

Hepatocellular carcinoma (HCC) is one of the leading causes of cancer death in the world. HCC accounts for more than 80 percent of liver carcinomas. There is a wide variation in the incidence of HCC in different parts of the world, and a number of factors have been identified as being of potential importance in the etiology of this disease (*Harrison's Principles of Internal Medicine*, Petersdorf, R. G., et al., McGraw-Hill, NY (1983), pp. 1816–1818). Chronic liver disease appears to predispose individuals toward HCC. There is accumulating epidemiological, serological, and molecular biological evidence linking chronic hepatitis B virus (HBV) infection to acquisition of human hepatocellular carcinoma (HCC). Since there are high HBV chronic carrier rates in many parts of the world, especially in Asia and Africa, HCC is one of the most common human malignancies (Beasley, R. P., *Hepatology* 2:215–265 (1982)). Mycotoxins, present in certain foodstuffs are also thought to predispose an individual toward HCC. Since liver cancer occurs 2–4 times more frequently in men than in women, hormonal factors may be important in the etiology of HCC. The course of HCC is usually rapid, with death resulting within 3–6 months, if the disease is not treated. Although it is, in some circumstances, possible to surgically remove the hepatic lesion, the 5-year survival of hepatoma patients is low. Despite the preponderance of HCC, there has only recently been progress in elucidating the mechanisms of malignant hepatocyte transformation at either the cellular or molecular level.

Present methods of detecting hepatomas rely upon the detection and identification of carcinoma-associated cell surface antigens (Hu, C. P., et al., *Hepatology* 6:1396–1402 (1986)), upon changes in the expression of alpha-fetoprotein (Liaw, Y. F., et al., *Liver* 6:133–137 (1986)), and by the accumulation of radioisotopic compounds (Lubbers, P. R., et al., *Amer. J. Radiol.* 148:1105–1108 (1987)). A review of the methods for detecting and diagnosing liver cancer is provided by Okuda, K. (*Dig. Dis. Sci.* 31:133s–146s (1986)).

C. LUNG CANCER

Lung cancer is among the leading causes of death in the United States, and throughout the world. Moreover, the incidence of this disease appears to be increasing (*Harrison's Principles of Internal Medicine*, Petersdorf, R. G., et al., McGraw-Hill, NY (1983), pp. 1572–1580). The overall 5-year survival for affected individuals (approximately 30–50 percent) has not changed significantly over the past 25 years.

Primary lung carcinomas have been divided into four classes, which are found with similar frequency in effected individuals. These classes are designated "small-cell carcinoma," and squamous carcinoma, epidermoid carcinoma, and adenocarcinoma (the latter three carcinomas also being referred to as "non-small-cell" carcinomas. Less than one percent of individuals having small-cell carcinoma survive five years after the diagnosis of the disease. In contrast, approximately one third of individuals having non-small-cell carcinoma will survive for at least five years after the diagnosis of the disease.

Small cell carcinomas are presently treated by combinations of surgical resection, radiation therapy and chemotherapy. Despite such aggressive treatments, the prognosis of the disease is extremely poor. The treatment of choice for non-small-cell carcinoma of the lung involves surgical resection of the cancerous lesion. Unfortunately, such surgical operations are possible only in the earliest stages of the disease. Although radiation therapy can be applied to treat non-small-cell carcinomas in latter stages, the prognosis of this therapy is poor.

The diagnosis and detection of lung cancers is facilitated by X-ray analysis of the lungs, by radioactive imaging, and through the detection of cell surface antigens which are associated with such lesions (Cuttitta et al., *Proc. Natl. Acad. Sci., USA* 78:4591 (1981)).

D. COLON AND RECTAL CARCINOMAS

Colon and rectal cancers accounts for approximately 20% of all deaths due to malignant disease in the United States. The cause of colorectal carcinoma, which affects men and women approximately equally, is not known. Despite advances in management of colorectal cancer, the death rate for this disease is the same today as it was 40 years ago. The most significant factor in the poor prognosis for colorectal carcinoma is delay in diagnosing the disease. Because symptoms of colorectal carcinoma are frequently vague and nonspecific in the early stages of the disease, detection is often delayed. As a result, the cancer is often so well established by the time a positive diagnosis is made that a cure is difficult or impossible. Thus, for example, patients whose tumor is confined to the bowel wall generally have an excellent chance for cure following surgical resection (five-year survival rate >95%). Where the tumor has extended to the serosa and mesenteric fat, however, the five-year survival rate following resection declines to 80%. Lymph node metastases reduce the five-year survival rate to 40%, while distant metastases (e.g., liver, lung, bone, brain) reduce the five-year survival rate to zero.

Commonly used screening tests for colorectal carcinoma contribute to delayed detection of the disease. For example, the guaiac test, which detects occult blood in the stool, requires that a colonic malignancy be advanced to the bleeding stage before it can be detected. Moreover, this test suffers from low and variable sensitivity due to dye instability. Sigmoidoscopy requires that any colorectal carcinoma be visible, and diagnosis may be complicated by the presence of other lesions such as hemorrhoids, polyps, and proctitis. Colonoscopy has similar drawbacks.

The inadequacies of presently available screening methods may be one reason that many colorectal cancers are first diagnosed as a result of a complication of the original lesion. For example, a bowel wall may be perforated by the tumor, causing acute peritonitis. Obviously, in such a case, the cancer will be well advanced by the time a diagnosis is made.

Delayed detection, then, is a major factor contributing to an overall five-year survival rate of only approximately 50% for colorectal malignancies. The diagnosis and treatment of colorectal cancer is described in LaMont et al., "Disease of the Small and Large Intestine," In: Petersdorf et al., eds., *Harrison's Principles of Internal Medicine*, 10th Edition, McGraw Hill, Publisher, New York, pp. 1762–1765 (1983).

Colorectal carcinomas generally respond poorly to chemotherapy. Although palliation may be effected, chemotherapy has not been shown to prolong the lives of patients diagnosed as having colorectal cancer, especially when the disease is widely disseminated. DeVita, "Principles of Cancer Therapy," In: *Harrison's Principles of Internal Medicine*, supra at 783 and Table 125–7.

The potential specificity of monoclonal antibodies for antigenic determinants associated with human tumor cells has led researchers and clinicians to investigate monoclonal antibodies for diagnostic and therapeutic use in the management of colorectal cancer. The potential clinical usefulness of monoclonal antibodies includes the detection of human cancers by immunohistochemistry (Gatter et al., *Semin. Oncol. IX*:517–525 (1982); Herlyn et al., *Proc. Natl. Acad. Sci., USA* 76:1438–1442 (1979)), radioimaging (Neville et al., *Hum. Pathol.* 13:1076–1081 (1982)), and the use of monoclonal antibodies as therapeutic agents (Levy et al., *Ann. Rev. Med.* 34:107–110 (1983)).

For example, Sakamoto et al. (European Patent Publication No. 0 119 556 A2), disclose the use of a panel of monoclonal antibodies raised in mice immunized with human gastrointestinal tumors to diagnose the presence of colon cancer. These monoclonal antibodies recognize antigenic determinants present on normal as well as cancerous gastrointestinal cells. Although it is stated that these monoclonal antibodies can be used to treat gastrointestinal tumors, the significant cross-reactivity of these monoclonal antibodies with normal tissue minimizes their therapeutic utility. The antigens recognized by this panel of monoclonal antibodies were either glycoproteins or glycolipids having molecular weights of 25 Kd, 29 Kd, 52 Kd, or 95 Kd. Four of the 12 monoclonal antibodies were of class IgM. The IgM monoclonal antibody showing the best reactivity with colon carcinoma cells (12/17) cross-reacted with pancreatic cancer, breast cancer, ovarian cancer, and lung cancer cells. Moreover, it cross-reacted with normal adult tissue from lung, liver, gallbladder, esophagus, colon, pancreas, ureter, breast, prostate, sweat glands, and secretions.

Lindholm et al., *Intl. Arch. Allergy Appl. Immunol.* 71:178 (1983), immunized mice with a colorectal adenocarcinoma cell line for liver metastasis membranes from a patient having colon adenocarcinoma to produce monoclonal antibodies. Three monoclonal antibodies of class IgM were identified that reacted with colorectal adenocarcinoma cell lines, extracts of pooled adenocarcinomas and individual gastro-intestinal tumors, but not with other cell types. The antigen complex was identified as a monosialoganglioside, but the antigen was not characterized further.

Koprowski et al., U.S. Pat. No. 4,349,528, describe the production of a monoclonal antibody specific for commercial carcinoembryonic antigen (CEA) having a molecular weight of about 180 Kd. The monoclonal antibody did not bind to antigens of colorectal carcinoma cells having molecular weights other than 180 Kd.

Sakamoto et al., *Fed. Proc.* 44(3):792 (Abstract 2222) (1985), describe antigens from human colon carcinoma which reacted with monoclonal antibodies obtained by immunization with cultured human colon and pancreas carcinomas, or with lysates of colon cancer cells. Two of the antigens K-314 (gp170) and V-215 (gp140) were detected only on colon and a few lung cancer cell lines. Neither the class of monoclonal antibodies involved nor the individual specificities of these monoclonal antibodies with respect to the antigens is disclosed.

Herlyn et al., *Proc. Natl. Acad. Sci., USA* 76(3):1438 (1979), describe the detection of a colorectal carcinoma-specific antigen using monoclonal antibodies (1083–17 and 1116–56) detected 8/9 human colorectal carcinomas. No data are presented characterizing the physical or chemical characteristics of the antigen involved. Both monoclonal antibodies were of class IgM.

Magnani et al., *Science* 212:55 (1981), describe the partial characterization of an antigen present on colon carcinoma cells which reacts with a monoclonal antibody. The molecular weight of the antigen, which was not purified to homogeneity, was not determined, although it was concluded that the antigen was a monosialoganglioside based upon its chemical reactivity and susceptibility to certain enzymes. The antigen was also found in human meconium, a rich source of normal fetal glycolipids.

Steplewski et al., *Canc. Res.* 41:2723 (1981), describe the release of monoclonal antibody-defined antigens by human colorectal carcinoma and melanoma cells. Some of the antigens detected were released into the tissue culture, while others could not be detected in tissue culture supernatants. It is stated that a monosialoganglioside antigen was released by tumor cells, but not by normal colon tissue, and that this antigen was not found in the serum of normal individuals. However, the antigen is not characterized further. Three other monoclonal antibodies (NS-3a-22, NS-10, and NS-33a) reacted with a glycolipid antigen released by most colorectal carcinoma cells. Two of these (NS-33a and NS-10) were of isotype IgM.

Herlyn et al., *Intl. J. Cancer* 27:769 (1981), studied the complement-dependent cytotoxicity of four hybridoma cell lines (NS-10, NS-33a, NS-38a, and NS-38c), which produced colon carcinoma-specific antibodies of isotype IgM. These monoclonal antibodies showed complement-dependent cytotoxicity against colon carcinoma cells.

Chang et al., *Hybridoma* 1:37 (1981), describe the detection of a monoclonal antibody-defined colorectal carcinoma antigen using a solid-phase binding inhibition radioimmunoassay. Two of the monoclonal antibodies were reported to be specific for antigen present on colorectal carcinoma. This antigen could be extracted from colon carcinoma cells using 3M KCl and was a glycolipid.

The diagnostic use of monoclonal antibodies in colorectal carcinoma is reviewed by Lloyd, supra, and by Davis et al., In: Prasad et al., eds., *Novel Approaches to Cancer Chemotherapy*, Academic Press, New York (1984) (see, e.g., Table III at page 43, setting forth tumor-associated antigens of gastrointestinal and colorectal tumors (among others) identified by various investigators.

As the above discussion demonstrates, despite longstanding scientific interest in the development of antibodies which are capable of recognizing antigens that are associated with human hepatoma, adenocarcinoma, and colorectal carcinoma cells, a need has continued to exist for an antibody that shows a high degree of specificity for these cells. Preferably, such an antibody should show no significant cross-reactivity with either normal human tissues or other malignant cell types.

SUMMARY OF THE INVENTION

The present invention relates to monoclonal antibodies which are capable of recognizing an antigen associated with hepatoma, adenocarcinoma of the lung, or colorectal carcinoma and to its uses in the diagnosis and treatment of colon adenocarcinoma.

In detail, the invention concerns a molecule capable of binding to an antigen of a hepatocarcinoma cell, selected from the group consisting of AF-20 and XF-8.

The invention further pertains to a hybridoma cell line capable of secreting a monoclonal antibody, the antibody being capable of binding to an antigen, consisting of AF-20 and XF-8, of a hepatocarcinoma cell.

The invention also pertains to a hapten capable of binding to an antibody, the antibody being capable of binding an antigen, consisting of AF-20 and XF-8.

The invention also provides in situ, in vivo, and in vitro detection methods capable of determining whether an animal contains an adenocarcinoma cell selected from the group consisting of a colon adenocarcinoma cell, a liver adenocarcinoma cell, and a lung adenocarcinoma cell, the method comprising:

A. contacting tissue of the animal that is suspected of containing the cell with a detectably labeled molecule capable of binding to an antigen, consisting of AF-20 and XF-8; and B. detecting any of the molecule bound to the antigen.

The invention also provides a method of suppressing the growth of an adenocarcinoma cell, the cell selected from the group consisting of a colon adenocarcinoma cell, a liver adenocarcinoma cell, and a lung adenocarcinoma cell in an animal which comprises administering to the animal a therapeutically effective amount of a molecule capable of binding to an antigen of the cell, wherein the antigen is AF-20 and XF-8.

The invention also provides a method for determining the presence of colorectal carcinoma in patients suffering from inflammatory bowel diseases, in general, and ulcerative colitis, and intestinal polyps, in particular.

BRIEF DESCRIPTION OF THE FIGURES

FIG. 5 is an autoradiograph which demonstrates the expression of XF-8 antigen on various malignant and normal tissues.

FIG. 8 is an autoradiograph which demonstrates the expression of AF-20 antigen on various tissues.

FIGS. 9A and 9B are autoradiographs which demonstrate the expression of AF-20 antigen on various tissues.

DESCRIPTION OF THE PREFERRED EMBODIMENTS

I. OVERVIEW OF THE PRESENT INVENTION

Figure 1A:
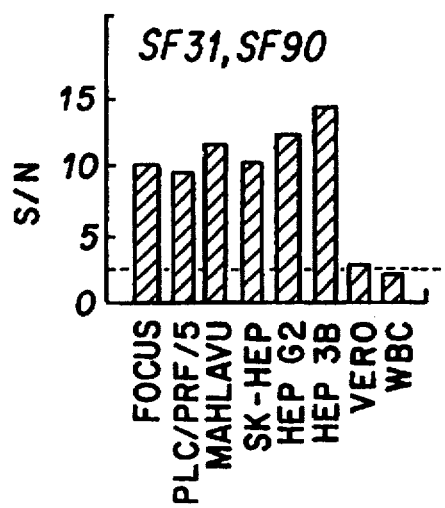
FIGS. 1A, 1B, 1C, 1D, 1E and 1F shows the indirect binding of antibodies to six HCC-derived cell lines, to green monkey kidney cells (Vero), and to normal white blood cells (WBC). Significant binding ( - - - ) is at a signal-to-noise ratio greater than 2.5 (*: not tested).
Figure 1B:
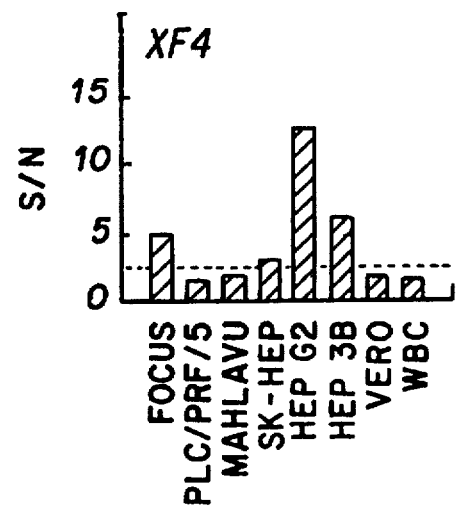
Figure 1C:
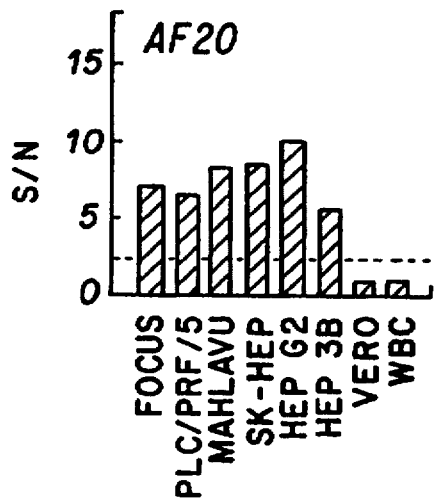
Figure 1D:
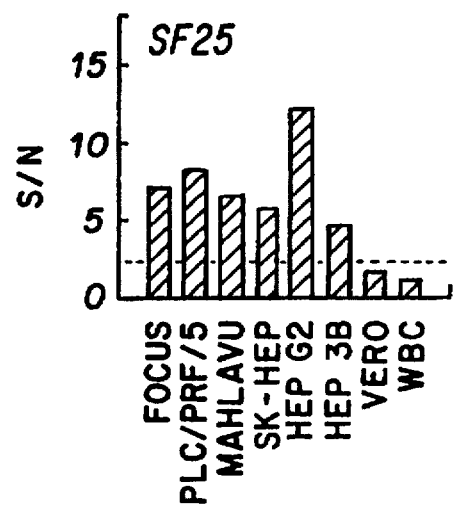
Figure 1E:
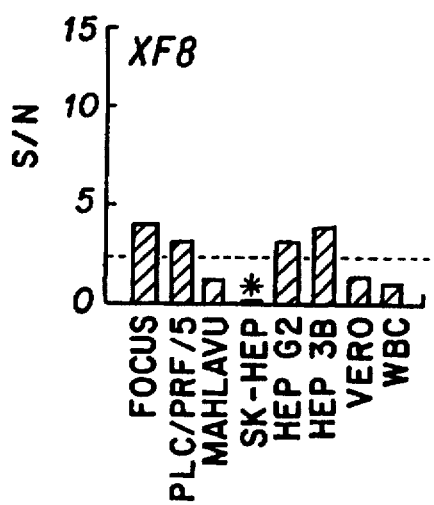
Figure 1F:
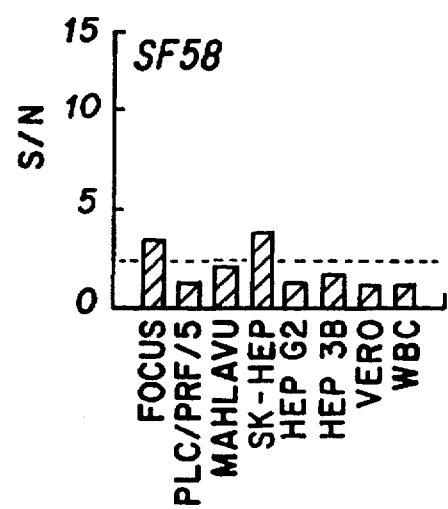

The present invention derives from the discovery of novel antigens designated AF-20 and XF-8 that are expressed on the surface of a human hepatocarcinoma cell. These antigens have been found to be associated (i.e. to be characteristic or diagnostic of) hepatoma, lung adenocarcinoma or colorectal carcinoma cells. The capacity to identify cells which express these antigens, and the capacity to bind these antigens with antibodies or fragments of antibodies, provide a method for diagnosing the presence of such adenocarcinomas. In addition, the discovery of these antigens and antibodies provides a method for suppressing the growth of such malignant cells.

One method of studying the transformed phenotype is to search for and characterize alterations in the antigenic composition of the cell surface. For this purpose, a large library of antibodies reactive against a HCC cell line can be prepared. Although any suitable HCC cell line can be employed for this purpose, it is preferable to employ the FOCUS HCC cell line. The FOCUS cell line was derived from a human hepatocellular carcinoma (Lun, H., et al., In Vitro 20:493–504 (1984)).

Antibodies which preferentially bind the HCC-derived cells can then be selected for use in a systematic analysis of antigenic variation in vivo between malignant and normal human liver tissue. In order to control for antigenic variation between individuals, it is preferable to employ paired sets of HCC and adjacent non-transformed liver tissue from South African hepatoma patients. The levels of antigen expression on these paired sets of tissue can preferably be studied using immunoperoxidase staining and a radioimmunoassay which measures binding of monoclonal antibodies to antigens on cell membranes. Antigens may then be further characterized by Western immunoblotting, metabolic labeling, and immunoprecipitation, etc.

The novel antigens of the present invention can be purified to be substantially free of natural contaminants through the use of any of a variety of methodologies. As used herein, a compound (such as an antibody, an antigen, a hapten, or fragments of such molecules) is said to be "substantially free of natural contaminants" if it has been substantially purified from materials with which it is normally and naturally found. The antigens of the present invention may be purified through application of standard chromatographic separation technology. Alternatively, and more preferably, the antigens of the present invention may be purified using immunoaffinity chromatography (Rotman, A., et al., *Biochim. Biophys. Acta* 641:114–121 (1981); Sairam, M. R., *J. Chromatog.* 215:143–152 (1981); Nielsen, L. S., et al., *Biochemistry* 21:6410–6415 (1982); Vockley, J., et al., *Biochem. J.* 217:535–542 (1984); Paucha, E., et al., *J. Virol.* 51:670–681 (1984); Chong, P., et al., *J. Virol. Meth.* 10:261–268 (1985)).

II. THE ANTIGENS AND ANTIBODIES OF THE PRESENT INVENTION, AND THEIR FUNCTIONAL DERIVATIVES

A. Immunological Considerations

In the following description, reference will be made to various methodologies well-known to those skilled in the art of immunology. Standard reference works setting forth the general principles of immunology include the work of Klein, J. (*Immunology: The Science of Cell-Noncell Discrimination*, John Wiley & Sons, New York (1982)); Kennett, R., et al. (*Monoclonal Antibodies, Hybridoma: A New Dimension in Biological Analyses*, Plenum Press, New York (1980)); Campbell, A. ("Monoclonal Antibody Technology," In: *Laboratory Techniques in Biochemistry and Molecular Biology*, Volume 13 (Burdon, R., et al., eds.), Elsevier, Amsterdam (1984)); and Eisen, H. N., (In: *Microbiology*, 3rd Ed. (Davis, B. D., et al., Harper & Row, Philadelphia (1980)).

An antibody is said to be "capable of binding" a molecule if it is capable of specifically reacting with the molecule to thereby bind the molecule to the antibody. As used herein, the term "hapten" is intended to refer to any molecule capable of being bound by an antibody. The term "epitope" is meant to refer to that portion of a hapten which can be recognized and bound by an antibody. A hapten or antigen may have one, or more than one epitope. An "antigen" is a hapten which is additionally capable of inducing an animal to produce antibody capable of binding to an epitope of that antigen. The specific reaction referred to above is meant to indicate that the hapten will react, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab')$_2$ fragments) which are capable of binding a hapten. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)).

B. The Antigens of the Present Invention, and Their Functional Derivatives

The present invention pertains to intact, substantially purified antigens which are capable of binding to the above-discussed antibodies. As will be readily appreciated by those of skill in the art, the purified antigens of the present invention may be fragmented to produce "functional derivatives" useful in accordance with the methods of the present invention. Additionally, purified antigen (or fragments thereof) may be analyzed to determine their amino acid sequence. The availability of such sequence information permits the production of antigens of the present invention (or fragments thereof) by synthetic chemical techniques.

As used herein, a "functional derivative" of the novel antigens of the present invention is a compound which possesses a biological activity (either functional or structural) that is substantially similar to a biological activity of the natural antigen. A molecule is said to be "substantially similar" to another molecule if both molecules have substantially similar structures or if both molecules possess a similar biological activity. The "functional derivatives" of the antigens of the present invention include both "fragments" and "variants" of the natural antigen. An antigen "fragment" is meant to refer to any polypeptide subset of that antigen. An antigen "variant" is meant to refer to a molecule substantially similar in structure to either the natural antigen, or to a fragment thereof provided that the "variant" has at least one biological activity that is either similar or inhibitory to an activity of the natural antigen. Thus, provided that a molecule possesses at least one biological activity that is either similar or inhibitory to an activity of one of the antigens of the present invention, it is considered a "variant" of the antigen, as that term is used herein, even if the molecule contains one or more amino acids not found in the antigen or antigen fragment, or if the sequences of amino acid residues in the variant and the natural antigen (or antigen fragment) are not identical.

C. The Antibodies of the Present Invention, and Their Functional Derivatives

The antibodies of the present invention may be prepared by any of a variety of methods. For example, cells expressing one of the antigens of the present invention (or fractions, lysates, etc. thereof) can be administered to an animal in order to induce the production of sera containing polyclonal antibodies that are capable of binding the antigen. In a preferred method, a preparation of one of the novel antigens of the present invention is prepared and purified to render it substantially free of natural contaminants. Such a preparation is then introduced into an animal in order to produce polyclonal antisera of greater specific activity.

In the most preferred method, the antibodies of the present invention are monoclonal antibodies (or hapten binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563–681 (1981)). In general, such procedures involve immunizing an animal (preferably a mouse) with one of the novel antigens of the present invention or, more preferably, with a cell which expresses such an antigen. Although any such cell may be employed in accordance with the present invention, it is preferable to employ the hepatocellular carcinoma cell line, FOCUS (Lun, H., et al., In Vitro 20:493–504 (1984)). The FOCUS cell line, which is derived from a human hepatocarcinoma would not be expected to secrete large amount of mucin glycoproteins (Lun, H., et al., In Vitro 20:493–504 (1984)). Suitable cells can be recognized by their capacity to bind antibody that is known to be capable of binding the antigens of the present invention. Such cells may be cultured in any suitable tissue culture medium; however, it is preferable to culture cells in Earle's modified Eagle's medium supplemented with 10% fetal bovine serum (inactivated at 56° C.), and supplemented with 10 µg/l of nonessential amino acids, 1,000 U/ml of penicillin, and 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium. Hybrids were cloned twice successively, at or beyond limiting dilutions (using Poisson statistics) on BALB/c or 3T3 monolayers. Second clonings were carefully examined to assure that clones established were the progeny of single cells. Subsequently, ascites fluid was collected after malignant growth of cloned hybrids in syngenic mice.

Hybrids and clones which secreted antibody were cultured in complete medium, and frozen and stored under liquid nitrogen in complete medium containing 25% fetal calf serum and 8% dimethylsulfoxide. The hybridoma cells obtained through such a selection are then assayed to identify clones which secrete antibodies capable of binding to the antigens of the present invention.

Alternatively, additional antibodies capable of binding to the novel antigens of the present invention may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, antibodies capable of binding one of the antigens of the present invention are used to immunize an animal. The splenocytes of such an animal are then used to produce hybridoma cells, and the hybridoma cells are screened to identify clones which produce antibody whose ability to bind to antibody (specific for the antigen) can be specifically blocked by the antigen. Such antibodies comprise anti-idiotypic antibodies to the antigens of the present invention. Such antibodies can be used to immunize an animal, and thereby induce the formation of antibody which are capable of binding to the antigens of the present invention. Since anti-idiotypic antibodies can be used to immunize an animal and thus provoke the production of antibodies reactive with the antigens of the present invention, they provide one method for inducing, or enhancing, an animal's immune response to liver, lung or colon cancer.

It will be appreciated that Fab and F(ab')$_2$ and other fragments of the antibody of the present invention may be used according to the methods disclosed herein for the detection and treatment of liver, lung or colon cancer in the same manner as intact antibody. Such fragments are typically produced by proteolytic cleavage, using enzymes such as papain (to produce Fab fragments) or pepsin (to produce F(ab')$_2$ fragments). Alternatively, hapten-binding fragments can be produced through the application of recombinant DNA technology or through synthetic chemistry.

Preferred cell lines, obtainable through the methods of the present invention, are those which produce antibody capable of binding to an antigen present on liver, lung and colon adenocarcinoma cells. The most preferred cell lines of the present invention are the monoclonal antibody-producing cell lines AF-20 and XF-8.

The AF-20 cell line produces monoclonal antibody AF-20 which is capable of binding to the AF-20 antigen. Cell line AF-20 was deposited under the provisions of the Budapest Treaty with the American Type Culture Collection 12301 Parklawn Drive, (ATCC), 12301 Parklawn Drive, Rockville, Md. 20852, on Apr. 12, 1988, and was given the ATCC designation: HB 9687.

The XF-8 cell line produces monoclonal antibody XF-8 which is capable of binding to the XF-8 antigen. Cell line XF-8 was deposited under the provisions of the Budapest Treaty with the American Type Culture Collection 12301 Parklawn Drive, (ATCC), 12301 Parklawn Drive, Rockville, Md. 20852, on Apr. 12, 1988, and was given the ATCC designation: HB 9686. Through application of the above-described methods, additional cell lines capable of producing antibodies which recognize epitopes of the novel antigens of the present invention can be obtained.

The above described procedures also permitted the isolation of a hybridoma cell line (designated SF-25) which produced an antibody that was capable of binding the SF-25 antigen of colorectal carcinoma cells. This cell line was deposited under the provisions of the Budapest Treaty with the American Type Culture Collection 12301 Parklawn Drive, (ATCC), 12301 Parklawn Drive, Rockville, Md. 20852, on Dec. 8, 1987, and was given the ATCC designation HB 9599.

III. ANTIGENS ASSOCIATED WITH CARCINOMA CELLS

A. Antigens Associated with Hepatocellular Carcinomas

Due to the recognized importance of cell surface molecules in regulating cell growth, replication, differentiation, and responsiveness to exogenous information and control (Reisfeld, R. A., and Cheriesh, D. A., *Adv. Immunol.* 40:323–350 (1987); Sulitzeana, D., *Adv. Cancer Res.* 44:1–36 (1986)), several recent studies of hepatic transformation have centered on generating monoclonal antibodies which recognize antigens present on HCC-derived cell lines. Furthermore, since cell surface antigenic variations may be manifestations of, and thus markers for, gene activation or inactivation, such an approach has the potential for eventually producing the tools necessary to elucidate some of the genetic changes associated with malignant transformation. This approach has led to the development of several antibodies which recognize HCC-associated antigens (Carlson et al., supra; Shouval, D., et al., *Hepatology* 5:346–356 (1985); Wiedmann, K. H., et al., *Hepatology* 7:543–550 (1987); Carlin, C. R., and Knowles, B. B., *Exp. Cell Res.* 147:359–367 (1983); Moriarity, D. M., et al., *Hybridoma* 2:39–47 (1983)).

The AF-20 and XF-8 antibodies of the present invention have been found to be capable of binding to an antigen associated with hepatocellular carcinoma. These antibodies appear to differ from the earlier reported HCC-selective monoclonal antibodies. Binding specificities, molecular weights, and competitive inhibition experiments have demonstrated that the three antibodies previously described by this laboratory (P215457, PM4E9917, and P232524) do not recognize the same antigens (Carlson, R. I., et al., *J. Clin. Invest.* 7–6:40–51 (1985); Shouval, D., et al., *Hepatology* 5:346–356 (19851). Two other earlier described antibodies (K-PLC2 and K-PLC3) show binding only to the PLC/PRF/5 cell line and probably also recognize dissimilar antigens (Wiedmann, K. H., et al., *Hepatology* 7:543–550 (1987)). Of the remaining three recently reported antibodies, 699B-C3 recognizes a 90 kDa membrane protein present on several cell lines (Carlin C. R., et al., *Exp. Cell Res.* 147:359–367 (19831) and 833-1C4 and K-PLC1 respectively recognize phospholipid and 115 kDa glycoprotein antigens present on HCC tissue and cell lines, but not on normal liver (Wiedmann, K. H., et al., *Hepatology* 7:543–550 (1987); Moriarity, D. M., et al., *Hybridoma* 2:39–47 (1983)). Insufficient specificity data have been reported to permit definitive comparisons between these antibodies and the ones reported here.

B. Antigens Associated with Human Colon, Liver, and Lung Carcinomas

The XF-8 and AF-20 antigens discussed above have been found to be common to human colon, liver, and lung adenocarcinoma cells. Thus, these antigens, and there functional derivatives, and antibodies reactive with these such compounds provide a means to diagnose, detect and treat these three adenocarcinomas.

IV. PRODUCTION OF THE ANTIGENS OF THE PRESENT INVENTION BY RECOMBINANT DNA TECHNOLOGY

The identification of the amino acid sequence of the antigens of the present invention (or their functional derivatives) permits these molecules to be produced through the application of recombinant DNA techniques. For example, an oligonucleotide can be constructed which is capable of encoding an antigen of the present invention (or its functional derivatives). Such an oligonucleotide can be operably linked into an expression vector and introduced into a host cell to enable the expression of the antigen (or functional derivatives of this antigen) by that cell. Techniques for synthesizing such oligonucleotides are disclosed by, for example, Wu, R., et al., *Prog. Nucl. Acid. Res. Molec. Biol.* 21:101–141 (1978)). Procedures for constructing recombinant molecules in accordance with the above-described method are disclosed by Maniatis, T., et al., In: *Molecular Cloning: A Laboratory Manual*, Cold Spring Harbor Press, Cold Spring Harbor, N.Y. (1984), which reference is herein incorporated by reference.

The identification of the amino acid sequence of an antigen of the present invention antigen, or fragments of such an antigen, also permits the cloning of a gene sequence which encodes the antigen. Such a gene sequence may be composed of either genomic DNA or, more preferably cDNA.

Any of a variety of methods may be used to clone a gene sequence which encodes antigens of the present invention. One such method entails analyzing a shuttle vector library of cDNA inserts (derived from a cell that expresses the novel antigens of the present invention) for the presence of an insert which contains a gene sequence which is capable of encoding the antigen. Such an analysis may be conducted by transfecting cells with the vector, and then assaying for antigen expression. A preferred method for cloning a gene sequence which encodes antigens of the present Invention entails determining the amino acid sequence of the antigen molecule. Although it is possible to determine the entire amino acid sequence of the antigen molecule it is preferable to determine the sequence of peptide fragments of the molecule. If the peptides are greater than 10 amino acids long, this sequence information is generally sufficient to permit one to clone a gene sequence such as those which encode the novel antigens of the present invention.

To accomplish this task, antigen molecules are preferably purified from producer cells by monoclonal antibody affinity chromatography and isolated by preparative sodium dodecyl sulfate-polyacrylamide gel electrophoresis ("SDS-PAGE") and electroelution. The antigen molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). The resulting peptides are separated, preferably by reverse-phase HPLC, and subjected to amino acid sequencing. To accomplish this task, the protein is preferably analyzed by automated sequenators.

Once one or more suitable peptide fragments have been sequenced, the DNA sequences capable of encoding them are examined. Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). Using the genetic code, one or more different oligonucleotides can be identified, each of which would be capable of encoding the antigen peptides. The probability that a particular oligonucleotide will, in fact, constitute the actual antigen-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:12 (1985). Using the "codon usage rules" of Lathe, a single oligonucleotide, or a set of oligonucleotides, that contains a theoretical "most probable" nucleotide sequence capable of encoding the antigen's peptide sequences is identified.

Although occasionally an amino acid sequences may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the antigen peptide is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate a gene sequence which encodes the antigen (Maniatis, T., et al., *Molecular Cloning A Laboratory Manual*, Cold Spring Harbor Press, Cold Spring Harbor, N.Y. (1982).

A suitable oligonucleotide, or set of oligonucleotides, which is capable of encoding a fragment of the gene sequence which encodes the antigen (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the antigen. Single stranded oligonucleotide molecules complementary to the "most probable" antigen peptide encoding sequences can be synthesized using procedures which are well known to those of ordinary skill in the art (Belagaje, R., et al., *J. Biol. Chem.* 254:5765–5780 (1979); Maniatis, T., et al., In: *Molecular Mechanisms in the Control of Gene Expression*, Nierlich, D. P., et al., Eds., Acad. Press, NY (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Maniatis, T., et al. (In: *Molecular Cloning, A Laboratory Manual*, Cold Spring Harbor Laboratories, Cold Spring Harbor, N.Y. (1982)), and by Haymes, B. D., et al. (In: *Nucleic Acid Hybridization, A Practical Approach*, IRL Press, Washington, D.C. (1985)), which references are herein incorporated by reference. The source of DNA or cDNA used will preferably have been enriched for the gene sequence which encodes the antigen. Such enrichment can most easily be obtained from cDNA obtained by extracting RNA from cells, such as hepatoma cells, which produce high levels of the antigen. An example of such a cell is a FOCUS cell (Lun, H., et al., In Vitro 20:493–504 (1984)).

To identify and clone the gene sequence capable of encoding the novel antigens of the present invention, a DNA, or more preferably a cDNA, library is screened for its ability to hybridize with the oligonucleotide probes described above. Suitable DNA preparations (such as human genomic DNA) are enzymatically cleaved, or randomly sheared, and ligated into recombinant vectors. The ability of these recombinant vectors to hybridize to the above-described oligonucleotide probes is then measured. Vectors found capable of such hybridization are then analyzed to determine the extent and nature of the antigen sequences which they contain. Based purely on statistical considerations, a gene sequence capable of encoding any of the antigens of the present invention could be unambiguously identified (via hybridization screening) using an oligonucleotide probe having only 18 nucleotides.

Thus, in summary, the actual identification of antigens of the present invention permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe to identify and isolate a gene sequence capable of encoding the novel antigens of the present invention.

Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *Eur. Mol. Biol. Organ. J.* 2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985)).

In an alternative way of cloning a gene sequence which encodes the antigens of the present invention, a library of expression vectors is prepared by cloning DNA or, more preferably, cDNA (from a cell capable of expressing the antigen) into an expression vector. The library is then screened for members capable of expressing a protein which binds to antigen-specific antibody, and which has a nucleotide sequence that is capable of encoding polypeptides that have the same amino acid sequence as the antigen, or fragments thereof. In this embodiment, DNA, or more preferably cDNA, is extracted and purified from a cell which is capable of expressing the antigen. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing the antigens of the present invention in order to produce a prokaryotic genomic expression vector library. Procedures for preparing cDNA and for producing a genomic library are disclosed by Maniatis, T., et al. (*Molecular Cloning: A Laboratory Manual*, Cold Spring Harbor Press, Cold Spring Harbor, N.Y. (1982)).

The above-described expression vector genomic library is used to create a bank of host cells (each of which contains one member of the library). The expression vector may be introduced into the host cell by any of a variety of means (i.e., transformation, transfection, protoplast fusion, electroporation, etc.). The bank of expression vector-containing cells is clonally propagated, and its members are individually assayed (using an immunoassay) to determine whether they produce a protein capable of binding to antigen-specific antibody.

The expression vectors of those cells which produce a protein capable of binding to antigen-specific antibody are then further analyzed to determine whether they express the entire antigen (and thus contain a gene sequence capable of encoding the entire antigen), whether they express only a part of the antigen (and thus contain only a fragment of a gene sequence capable of encoding the antigen), or whether they express (and contain) a gene whose product, though immunologically related to one of the antigens of the present invention, is not such an antigen. Although such an analysis may be performed by any convenient means, it is preferable to determine the nucleotide sequence of the DNA or cDNA fragment which had been cloned into the expression vector. Such nucleotide sequences are then examined to determine whether they are capable of encoding polypeptides having the same amino acid sequence as digestion fragments of the antigen.

An expression vector which contains a DNA or cDNA molecule which encodes a gene sequence capable of encoding one of the antigens of the present invention may, thus, be recognized by: (i) the ability to direct the expression of a protein which is capable of binding to antigen-specific antibody; and (ii) the presence of a nucleotide sequence which is capable of encoding each of the fragments of the antigen. The cloned DNA molecule of such an expression vector may be removed from the expression vector and isolated in pure form.

V. EXPRESSION OF THE CLONED ANTIGEN ENCODING GENE SEQUENCES

The present invention therefore provides a means for obtaining a DNA molecule which contains a gene sequence capable of encoding each of the antigens of the present invention. By operably linking such a DNA molecule (or a fragment or mutated form of such a DNA molecule) to a functional promoter, it is possible to direct the expression of the antigen-encoding sequences (or a functional derivative thereof) in a cell, or organism.

The expression of a DNA sequence requires that the DNA sequence be "operably linked" to DNA sequences which contain transcriptional and translational regulatory information. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Regulatory regions in eukaryotic cells will in general include a promoter region sufficient to direct the initiation of RNA synthesis.

Two DNA sequences (such as a promoter region sequence and an antigen-encoding sequence) are said to be operably linked if the nature of the linkage between the two DNA sequences does not (1) result in the introduction of a frame-shift mutation, (2) interfere with the ability of the promoter region sequence to direct the transcription of the antigen-encoding sequence, or (3) interfere with the ability of the antigen-encoding sequence to be transcribed by the promoter region sequence. Thus, a promoter region would be operably linked to a DNA sequence if the promoter were capable of transcribing that DNA sequence.

To express the antigen molecule (or a functional derivative thereof) in a prokaryotic cell (such as, for example, *E. coli*, *B. subtilis*, *Pseudomonas*, *Streptomyces*, etc.), it is necessary to operably link the antigen-encoding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pPR325, etc. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)), the promoters of the bacteriophages of Bacillus (Gryczan, T. J., In: *The Molecular Biology of the Bacilli*, Academic Press, Inc., NY (1982)), and Streptomyces promoters (Ward, J. M., et al., *Mol. Gen. Genet.* 203:468–478 (1986)). Prokaryotic promoters are reviewed by Glick, B. R., (*J. Ind. Microbiol.* 277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell requires the presence of a ribosome binding site upstream of the gene-encoding sequence. Such ribosome binding sites are disclosed, for example, by Gold, L., et al. (*Ann. Rev. Microbiol.* 3–5:365–404 (1981)).

If expression is desired in a eukaryotic cell, such as yeast, fungi, mammalian cells, or plant cells, then it shall be necessary to employ a promoter capable of directing transcription in such a eukaryotic host. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); and the yeast gal4 gene promoter (Johnston, S. A., et al., *Proc. Natl. Acad. Sci. (USA)*. 79:6971–6975 (1982); Silver, P. A., et al., *Proc. Natl. Acad. Sci. (USA)* 81:5951–5955 (1984)).

As is widely known, translation of eukaryotic mRNA is initiated at the codon which encodes the first methionine of an oligonucleotide. For this reason, it is preferable to ensure that the linkage between a eukaryotic promoter and an oligonucleotide which encodes the antigen molecule (or a functional derivative thereof) does not contain any intervening codons which are capable of encoding a methionine (i.e., AUG). The presence of such codons results either in a formation of a fusion protein (if the AUG codon is in the same reading frame as the antigen-encoding oligonucleotide) or a frame-shift mutation (if the AUG codon is not in the same reading frame as the antigen-encoding gene sequence).

An oligonucleotide which encodes the antigen protein (or a functional derivative thereof) when operably linked to a functional promoter is preferably introduced into a recipient cell by any of a variety of suitable means: transformation, transfection, conjugation, protoplast fusion, electroporation, etc.

The antigen-encoding sequence and an operably linked promoter may be introduced into a recipient cell either as a non-replicating DNA (or RNA) molecule, which may either be a linear molecule or, more preferably, a closed covalent circular molecule. Since such molecules are incapable of autonomous replication, the expression of the antigen polypeptide may occur through the transient expression of the introduced gene sequence. Alternatively, permanent expression may occur through the integration of the introduced gene sequence into the host chromosome.

Preferably, the introduced gene sequence will be incorporated into a plasmid or vital vector capable of autonomous replication in the recipient host. Any of a wide variety of vectors may be employed for this purpose. Factors of importance in selecting a particular plasmid or vital vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Maniatis, T., et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, NY (1982), pp. 307–329). Suitable Streptomyces plasmids include pIJ101 (Kendall, K. J., et al., J. Bacteriol. 169:4177–4183 (1987)), and streptomyces bacteriophages such as ΦC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)).

Preferred eukaryotic plasmids include BPV, vaccinia, SV40, 2-micron circle, etc. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise, Vol. 3, Gene Expression*, Academic Press, NY, pp. 563–608 (1980)).

VI. DIAGNOSTIC USES OF ANTIBODIES AND ANTIBODY FRAGMENTS

The antibodies, or fragments of antibodies, of the present invention may be used to quantitatively or qualitatively detect the presence of cells which express the antigen. Thus, the antibodies (of fragments thereof) of the present invention may be employed in histology and biopsy to detect or visualize liver, lung or colon carcinomas. Such detection may be accomplished using any of a variety of immunoassays. For example, by radioactively labeling the antibodies or antibody fragments, it is possible to detect the antigen through the use of radioimmune assays. A good description of a radioimmune assay (RIA) may be found in *Laboratory Techniques and Biochemistry in Molecular Biology*, by Work, T. S., et al., North Holland Publishing Company, NY (1978), with particular reference to the chapter entitled "An Introduction to Radioimmune Assay and Related Techniques" by Chard, T., incorporated by reference herein. Alternatively, fluorescent, enzyme, or other suitable labels can be employed.

The detection of cells which express any of the antigens of the present invention may be accomplished by removing a sample of tissue from a patient and then treating the isolated sample with any of the suitably labeled antibodies (or antibody fragments) of the present invention. Preferably, such in situ detection is accomplished by removing a histological specimen from a patient, and providing the labeled antibody of the present invention to such specimen. The antibody (or fragment) is preferably provided by applying or by overlaying the labeled antibody (or fragment) to a sample of tissue. Through the use of such a procedure, it is possible to determine not only the presence of antigen, but also the distribution of the antigen on the examined tissue. Using the present invention, those of ordinary skill will readily perceive that any of a wide variety of histological methods (such as staining procedures) can be modified in order to achieve such in situ detection.

Alternatively, the detection of cells which express any of the antigens of the present invention may be accomplished by in vivo imaging techniques, in which the labeled antibodies (or fragments thereof) are provided to a patient, and the presence of the liver, lung, or colon carcinoma is detected without the prior removal of any tissue sample. Such in vivo detection procedures have the advantage of being less invasive than other detection methods, and are, moreover, capable of detecting the presence of antigen-expressing cells in tissue which cannot be easily removed from the patient.

The antibodies (or fragments thereof) of the present invention are also particularly suited for use in in vitro immunoassays to detect the presence of the antigens of the present invention in body tissue, fluids (such as blood, lymph, etc.), stools, or cellular extracts. In such immunoassays, the antibodies (or antibody fragments) may be utilized in liquid phase or bound to a solid-phase carrier.

In accordance with the above-discussed assays, antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$[In] is a preferred isotope. Its use may have substantial advantages since it avoids the problem of dehalogenation of the $^{125}$[I] or $^{131}$[I]-labeled monoclonal antibody by the liver. In addition, this radionucleotide has a more favorable gamma emission energy for imaging (Perkins, A. C., et al., *Eur. J. Nucl. Med.* 10:296–301 (1985); Carasquillo, J. A., et al., *J. Nucl. Med.* 28:281–287 (1987)). For example, $^{111}$[In] coupled to monoclonal antibodies with 1-(P-isothiocyanatobenzyl)-DPTA have shown little uptake in non-tumorous tissues, particularly the liver and therefore enhance specificity of tumor localization (Esteban, J. M., et al., *J. Nucl. Med.* 28:861–870 (1987)).

Examples of suitable non-radioactive isotopic labels include $^{157}$Gd, $^{55}$Mn, $^{162}$Dy, $^{52}$Tr, $^{56}$Fe, etc.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta* 70:1–31 (1976)), and Schurs, A. H. W. M., et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The detection of the antibodies (or fragments of antibodies) of the present invention can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The binding molecules of the present invention may also be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., blood, lymph, liquified stools, tissue homogenate, etc.) and a quantity of detectably labeled soluble antibody is added to permit detection and/or quantitation of the ternary complex formed between solid-phase antibody, antigen, and labeled antibody.

Typical immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. Such "two-site" or "sandwich" assays are described by Wide at pages 199–206 of *Radioimmune Assay Method*, edited by Kirkham and Hunter, E. & S. Livingstone, Edinburgh, 1970.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

As explained above, the immunometric assays for antigen require that the particular binding molecule be labeled with a "reporter molecule." These reporter molecules or labels, as identified above, are conventional and well-known to the art. In the practice of the present invention, enzyme labels are a preferred embodiment. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, beta-galactosidase, urease, glucose oxidase, glycoamylase, malate dehydrogenase, and glucose-6-phosphate dehydrogenase. Urease is among the more preferred enzyme labels, particularly because of chromogenic pH indicators which make its activity readily visible to the naked eye.

The above-described in situ, in vitro, or in vivo detection methods may be used in the diagnosis of liver, lung, or colon carcinoma. Additionally, such detection methods may be used to assist in the determination of the stage of a malignancy, or to determine whether an individual possesses malignant lesions, which may be obscured (or whose detection may be complicated) by the close association of normal tissue.

One especially preferred use for the antibodies (and antibody fragments) of the present invention is as an aid in the diagnosis of colon cancer in patients who present with symptoms of inflammatory bowel diseases, and in particular, ulcerative colitis or intestinal polyps. Using the methods of the prior art, the early diagnosis and detection of colon cancer in individuals suffering from such inflammatory bowel disease is often complicated, or masked, by the symptoms of bowel disease. Thus, concern that an occult colorectal carcinoma may be present in an individual suffering from inflammatory bowel disease may result in a recommendation that such individuals submit to a colectomy. Because the antibodies (and antibody fragments) of the present invention are capable of identifying colorectal carcinomas, they can be used to determine the presence of otherwise occult lesions. Thus, their use in the diagnosis of the cause and severity of inflammatory bowel disease and colorectal carcinoma is capable of preventing unwarranted colectomies, and is, therefore, highly desirable.

VII. DIAGNOSTIC USES OF THE ANTIGENS OF THE PRESENT INVENTION, AND THEIR FUNCTIONAL DERIVATIVES

The present invention also provides a method for detecting the presence of antibodies which are specific to (i.e. capable of binding to) one of the antigens of the present invention. The presence of such antibodies in the sera of an animal would be indicative of that animal's prior or present exposure to cells expressing the antigen. Thus, this method provides an alternative diagnostic test for the cancer associated with the presence of such antigen. Such a diagnostic test could be performed using either purified intact antigen, a functional derivative of the intact antigen or an antibody which was anti-idiotypic to an antigen-specific antibody. Fragments of such an idiotypic antibody could also be employed. Such molecules are preferably labeled (using any of the enzyme, radioisotopic, non-radioactive isotopic, fluorescent or chemiluminescent labels described above. Such an immunoassay may be performed by adapting the method of Fridlender, B. R. (U.S. Pat. No. 4,313,927). Thus, purified antigen or hapten (or anti-idiotypic antibody or fragments of such an antibody) is coupled or bound to a solid surface. Any of a variety of known coupling techniques may be modified to accomplish this goal. The immobilized surface to which these molecules are bound may be chosen from a wide variety of possible surfaces such as nylon, latex, glass, silica, polyethylene, polystyrene, polyvinylchloride or polycarbonate. The support material may have virtually any possible structural configuration so long as the coupled molecule is capable of binding to any antigen-specific antibody which is provided. Thus, the support configuration may be spherical, as in a bead, or cylindrical, as in the inside surface of a test tube, or the external surface of a rod. Alternatively, the surface may be flat such as a sheet, test strip, etc.

In one embodiment, a biological sample (such as, for example, blood, lymph, etc.) is assayed in the manner described above, to determine whether antigen-specific antibodies are present. In an alternative embodiment, a biological sample (such as a biopsy of tissue) is introduced into a test animal (such as, for example, a mouse) and the sera of the animal analyzed to determine whether antibodies recognizing the antigen have been elicited. Alternatively, the biological sample could be provided to splenocyte cells grown in tissue culture, and the resulting antibodies analyzed for their ability to bind antigen. Any of the many known immunoassay techniques may be modified in accordance with these embodiments.

As used herein, an effective amount of a diagnostic reagent (such as an antibody, antibody fragment, or hapten) is one capable of achieving the desired diagnostic discrimination. The amount of such materials which are typically used in a diagnostic test are generally between 0.01–1 µg, and preferably between 0.1–1 µg.

VIII. THERAPEUTIC USES OF THE PRESENT INVENTION

In addition to providing a method for diagnosing certain cancers, the present invention also provides a means for preventing the onset of such cancers, and for treating infected animals, including humans. The discovery that the antigens of the present invention are expressed on lung, liver, or colon cancer cells, and the identification of antibodies capable of binding to such antigens provides means for preventing and treating these cancers. In one embodiment, the antigen, an immunologically active fragment of this antigen, or an anti-idiotypic antibody, or fragment thereof is provided to an animal to thereby elicit the production of antibodies capable of recognizing antigen-expressing cells.

The ability to label antibodies, or fragments of antibodies, with toxin labels provides an additional method for treating lung, liver, or colon cancer. In this embodiment, antibodies, or fragments of antibodies which are capable of recognizing the antigens associated with such cancers are labeled with toxin molecules and administered to a patient suspected of having such cancer. When such a toxin derivatized molecule binds to a cancer cell, the toxin moiety will cause the death of the cancer cell.

Any of a variety of toxin molecules may be employed to produce such labeled antibodies or labeled antibody fragments. Examples of suitable toxin labels include diphtheria toxin, ricin, and cholera toxin, etc. One preferred type of toxin molecule is a "photo-activatable toxin molecule." Examples of such "photo-activatable toxin molecules" include Photofrin II (Williams, R. D., et al., *Photochem. Photobiol.* 46:733–738 (1987); Mattielli, J., et al., *Photochem. Photobiol.* 46:873–880 (1987)), hematoporphyrin derivatives (Benson, R. C., *Urology* 31:13–17 (1988)), hemoglobin, and its derivatives (Polla, L. L., et al., *Ann. Dermatol. Venereol.* 114:497–505 (1987)); procion blue (Macklis, J. D., et al., *Brain Res.* 359:158–165 (1985)), fluorescent, and other dyes (Miller, J. P., et al., *Science* 206:702–704 (1979); Manyak, M. J., et al., *J. Clin. Oncol.* 6:380–391 (1988)), etc. The critical attribute of such molecules is that they be capable of greater absorption of light (at some wavelength) than the surrounding tissue.

In this therapy, termed "photothermolysis," photoactivation of the toxin is achieved by a careful selection of wavelength, pulse, and intensity of the light. The light energy absorbed by such molecules is released either as heat or emitted as light at a different wavelength. If a suitable light (such as, preferably, a laser light) is employed, the death of cells and tissue which contain the photo-activatable toxin will occur, either because of the amount of the heat released by this process, or because of the photo-oxidation of essential biological molecules in the cells or tissue by the emitted light. The physics of laser therapy and photothermolysis are reviewed by Hobbs, E. R., et al. (*J. Dermatolog. Surg. Oncol.* 13:955–964 (1987)), Anderson, R. R., et al. (*Science* 220:524–527 (1983)), Macklis, J. D., et al. (*Brain Res.* 359:158–165 (1985)), Wilson, B. C. (*Phys. Med. Biol.* 31:327–360 (1986)) and especially by Manyak, M. J., et al. (*J. Clin. Oncol.* 6:380–391 (1988)), all of which references are herein incorporated by reference.

By conjugating the antibodies of the present invention with a photo-activatable toxin, it is possible to direct the toxin molecule only to those cells which express a corresponding tumor-associated antigen. This method has been used to provide a selective means for treating a tumor without damage to normal (i.e. non-antigen expressing) cells. Examples of the use of this method are provided by Mew, D., et al. (*Cancer Res.* 45:4380–4386 (1985); *J. Immunol.* 130:1473–1477 (1983)); by Wat, C.-K., et al. (In: *Prog. Clin. Biol. Res.* Vol 170, (Doiron, D. R., et al., eds.), Alan R. Liss, NY, pp. 351–360 (1984)); and by Oseroff, A. R., et al. (*Photochem. Photobiol.* 46:83–96 (1987); *Photochem. Photobiol.* 43 *Suppl.*:105s (1986); Photochem. Photobiol. 41 *Suppl.*:75s (1985); *Photochem. Photobiol.* 41 *Suppl.*:35s (1985); *Proc. Natl. Acad. Sci. (USA)* 8–3:8744–8748 (1986); Clin Res. 33:674a (1985); *J. Invest. Dermatolog.* 8–4:335 (1985); all of which references are herein incorporated by reference).

The above-described photothermolysis therapy can be accomplished using any light source which is capable of photo-activating the toxin. The photo-activation of such toxins can thus be achieved using light sources other than lasers. For example, such photo-activation can be achieved using light from an ordinary light bulb (Dougherty, T. J., et al., *J. Natl. Canc. Inst.* 55:115–129 (1979); Wilson, B. C., *Phys. Med. Biol.* 31:327–360 (1986)). Photo-activation of the toxin may alternatively be achieved by the administration of a chemiluminescent agent (i.e. a light-emitting molecule) to an individual who has received the photo-activatable toxin. This embodiment of the present invention is particularly advantageous in the in situ treatment of gastric carcinomas, intestinal polyps, Barrette's esophagus. The embodiment may also be used for metastatic cancers (Phillip, M. J., et al., In: Porphyrin Localization and Treatment of Tumors (Doiron, D. R., et al., eds.), Alan R. Liss, NY, pp. 563–569 (1985)).

As would be understood by one of ordinary skill in the art, such compositions may contain salts, buffers, adjuvants, or other substances which are desirable for improving the efficacy of the composition. Adjuvants are substances that can be used to specifically augment a specific immune response. Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus Brucella. Among those substances particularly useful as adjuvants are the saponins such as, for example, Quil A. (Superfos A/S, Denmark). Examples of materials suitable for use in vaccine compositions are provided in *Remington's Pharmaceutical Sciences* (Osol, A., Ed., Mack Publishing Co., Easton, Penn., pp. 1324–1341 (1980)).

The therapeutic compositions of the present invention can be administered orally or parenterally by injection, rapid infusion, nasopharyngeal absorption intranasopharangeally), dermoabsorption. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage which can be adjusted by one of ordinary skill in the art needed to provide an effective amount of the composition will vary depending upon such factors as the animal's age, condition, sex, and extent of disease, if any, and other variables.

The antigenic preparations of the invention can be administered by either single or multiple dosages of an effective amount. Effective amounts of the compositions of the invention can vary from 0.01–1,000 µg/ml per dose, more preferably 0.1–500 µg/ml per dose, and most preferably 10–300 µg/ml per dose.

Having now generally described the invention, the same will be more readily understood through reference to the following examples which are provided by way of illustration; and are not intended to be limiting of the present invention, unless specified.

EXAMPLE 1

Production of Monoclonal Antibody Producing Hybridoma Cells

Mycoplasma-free cells (either FOCUS, PLC/PRF/5, SK Hep-1, Mahlavu, Hep G2, Hep 3B, or Vero cells) were harvested from monolayer cultures by washing with phosphate-buffered saline (PBS) followed by treatment with versene buffer in the absence of trypsin. White blood cells (WBC) were isolated from fresh human blood by Ficoll-hypaque centrifugation. Cells used in the binding assays were frozen in 15% glycerol and stored at −80° C. Hepatoma and adjacent non-transformed liver tissues were obtained from surgically resected or autopsy specimens from South Africa, frozen in liquid nitrogen, and stored at −80° C.

The hepatocellular carcinoma cell line FOCUS was used to immunize mice. The FOCUS cell lines was chosen since it appears to be a good model for studying HBV associated HCC on the basis of enzymatic and protein synthetic capabilities, solid tumor morphology, and the presence of a single HBV integration site (He, L., et al., In Vitro 20:493–504 (1984); Shih, C., et al., *J. Virol.* 61:3491–3498 (1987)). The monoclonal antibodies of the present invention were prepared against cells grown from the second passage of the FOCUS cell line in order to represent the antigenicity of the original primary HCC tumor as faithfully as possible. The cells were grown in Earle's modified Eagle's medium (M. A. Bioproducts, Walkerville, Md.) supplemented with 10% fetal bovine serum (inactivated at 56° C.), 10 µg/ml of non-essential amino acids, 1,000 U/ml of penicillin, and 100 µg/ml of streptomycin. An early passage of FOCUS cells from the original tumor had been kept in liquid nitrogen. This culture was subsequently regrown and harvested from monolayer culture. Cells were harvested from the monolayer cultures by washing three times with 20 mM phosphate-buffered saline (PBS), pH 7.2, followed by treatment with versene buffer in the absence of trypsin. The single cell suspensions, thus obtained, were used for immunization of Balb/c mice. Primary immunizations were accomplished intraperitoneally with $4.0 \times 10^6$ intact whole cells/ml in 50% complete Freund's adjuvant. After 6–10 weeks, secondary immunizations were performed by an intravenous inoculation of $4.0 \times 10^6$ cells in 200 µl of PBS. Three days later, mouse spleen cells were fused with either SP$_2$O, NS1, or X63 mouse myeloma cells using 30% polyethylene glycol. Hybridomas were selected and maintained as described by Wands, J. R., et al. (Gastroenterology 80:225–232 (1981)). Ascites fluid was prepared by injection of hybridoma cells intraperitoneally into 2, 6, 20, 14-tetramethylpentadecane (Pristane; Aldrich) primed BALB/c mice. Purification and iodination of monoclonal antibodies were performed as described by Wands, J. R., et al. (*Gastroenterology* 80:225–232 (1981)).

The hybridomas which were obtained through the above-described procedure were screened for antibody activity on a panel of cell lines listed in Table 1. Subsequent specificity testing of cloned hybridomas was performed against various cell lines by both indirect and direct binding radioimmunoassays (RIAs).

Homogenization was performed at 4° C. Sections (0.5–1.0 g) of frozen hepatoma and remote non-transformed liver tissue were homogenized with a Polytron (Brinkmann) in 10 ml of PBS (pH 7.2) containing 0.1% $NaN_3$ and centrifuged at 20,000× g for 30 min. The membrane pellet was re-homogenized in 10 ml of $PBS/NaN_3$ and centrifuged as above, then resuspended in 10 ml of $PBS/NaN_3$ with 20% glycerol and centrifuged at 1,000× g for 5 min. The fibrous layer was discarded and the protein concentration of the remaining membrane homogenate was determined by the method of Lowry (Lowry, O. H., et al., *J. Biol. Chem.* 193:265–275 (1951)). The membranes were frozen in liquid nitrogen, then stored at −80° C.

The indirect radioimmunoassay was carried out in 96 well filter-bottomed plates (V&P Scientific Inc., San Diego, Calif.). These plates were pre-incubated at room temperature with 250 µl of calf serum (for 15 min) or with 100 µl of bovine serum (for 30 minutes) in order to block non-specific protein binding sites in each well. Next, 1×10⁵ target cells (suspended in 100 µl of Earle's modified Eagle's medium and containing 20% fetal bovine serum) were incubated with 100 µl of fresh culture supernatant from 70% confluent hybridoma for 1 hour at room temperature with gentle agitation. Cells were drawn onto filters in the wells by suction, then washed three times with 0.2 ml of PBS containing 20% fetal bovine serum. Approximately, 50 µg of membrane homogenate protein or approximately 1×10⁵ cells were trapped in each filter. Indirect assays were performed by incubating each filter in 100 µl of monoclonal antibody solution (as a hybridoma supernatant or as a 1:200 dilution of ascites) for 1 hr. The filters were then washed with 10% calf serum/PBS containing 1×10⁵ cpm of $^{125}$[I]-labeled sheep anti-mouse IgF(ab')₂, and incubated with agitation. After 1 hour, the cells were again washed three times with PBS/20% fetal bovine serum and the filters were dried and counted using a gamma well counter.

TABLE 1

| Origin of Cell Lines | |
|---|---|
| Cell Line | Tissue of Origin |
| LS 180 | Human, Colon, Adenocarcinoma |
| COLO 320 | Human, Colon, Adenocarcinoma |
| SW 403 | Human, Colon, Adenocarcinoma |
| WiDr | Human, Colon, Adenocarcinoma |
| CaCo-2 | Human, Colon, Adenocarcinoma |
| SK-Co-I | Human, Ascites, Colon Adenocarcinoma |
| FOCUS | Human, Liver, Hepatoma |
| PLC/PRF/5 | Human, Liver, Hepatoma |
| MAHLAVU | Human, Liver, Hepatoma |
| Hep G2 | Human, Liver, Hepatoma |
| Hep 3B | Human, Liver, Hepatoma |
| SK-HEP-1 | Human, Ascites, Hepatoma |
| Chang Liver | Human, Liver, Epithelial-like morphology |
| A-427 | Human, Lung, Adenocarcinoma |
| SK-LU-1 | Human, Lung, Adenocarcinoma |
| Calu-3 | Human, Pleural effusion, Lung adenocarcinoma |
| BT-20 | Human, Breast, Adenocarcinoma |
| A-498 | Human, Kidney, Carcinoma |
| Caov-3 | Human, Ovary, Adenocarcinoma |

TABLE 1-continued

| Origin of Cell Lines | |
|---|---|
| Cell Line | Tissue of Origin |
| C-33A | Human, Cervix, Undifferentiated carcinoma |
| HeLa | Human, Cervix, Adenocarcinoma |
| SK-UT-1 | Human, Uterine, Mesodermal tumor |
| AN3 CA | Human, Endometrium, Adenocarcinoma |
| JEG-3 | Human, Choriocarcinoma |
| SK-MEL-5 | Human, Lymph node, Malignant melanoma |
| Vero | Monkey, Kidney, Fibroblast-like morphology |

A direct binding assay was performed by preincubating the cells or membranes for 15 min with a 1:100 dilution of either unlabeled relevant monoclonal antibody or unlabeled non-relevant antibody (B2TT, an anti-tetanus toxoid IgG). 1×10⁵ cpm of $^{125}$[I]-labeled monoclonal antibody diluted in 50% calf serum/PBS was then added. After 1 hr, the filters were washed and counted.

Monoclonal antibodies were labeled with $^{125}$[I] or $^{131}$[I] using the Iodogen method (Fraker, P. J., et al., *Biochem. Biophys. Res. Commun.* 80:849–857 (1978)) to a specific activity of between 5–15 µCi/µg. Briefly, 50 µl aliquots of Iodogen (1,3,4,6-tetrachloro-3α,6α-diphenylglycoluril; Pierce Chemical Co., Rockford, Ill.) at 50 µg/ml in chloroform were evaporated to dryness under nitrogen gas in 10×75 mm glass tubes. $Na^{125}$[I] or $Na^{131}$[I] (Amersham Corp., Searle Div., Arlington Heights, Ill.) and 100 µg of monoclonal antibody were added to the tubes, which were then incubated for 6 minutes at room temperature. The radiolabeled monoclonal antibody was then separated from free iodine on a PD-10 column (Pharmacia Fine Chemicals, Piscataway, N.J.) which had been previously equilibrated with 0.9% NaCl. Iodenated monoclonal antibodies were always tested to assure that there was no loss of their specificity or immunoreactivity by direct binding to FOCUS and other cell lines. Labeled monoclonal antibodies (1×10⁵ cpm) were incubated with 1×10⁵ cells in 100 µl of PBS/20% fetal bovine serum for 1 hour at room temperature. The cells were then washed three times as described above and the radioactivity of the dried filters was determined. $^{125}$[I]-labeled, non-relevant monoclonal antibody (designated B2TT (an anti-tetanus toxoid $IgG_1$ and $IgG_{2b}$)) was employed as a negative control. Only if the amount of radioactivity bound to antigen specific antibody was greater than 2.5 times that bound by the control antibody were the results considered to indicate positive binding values.

For indirect assays, the ratio of relevant to non-relevant monoclonal antibody binding was termed the signal-to-noise ratio (S/N). Direct assays were done in quadruplicate. Here, the specific binding was determined by subtracting radiolabeled antibody binding in the presence of unlabeled antibody (non-specific binding) from the binding in the presence of a non-relevant antibody (total binding). The standard deviations reported represent the sum of the standard deviations of the two binding values. P values were calculated using Student's t test to compare the significance of differences in mean binding values between tissues.

In the above-described experiments, immunoperoxidase staining was performed in the following manner. Frozen tissue specimens embedded in OCT (Miles Scientific) were sectioned, fixed to slides with −20° C. acetone, and equilibrated in PBS. The slides were stained with the Vectastain ABC kit (Vector Laboratories, Inc.). Briefly, the slides were incubated in dilute horse serum for 20 min, dried by blotting, then incubated overnight at 4° C. with monoclonal antibody (1:100–1:1000 ascites in PBS), followed by washing with PBS. The slides were sequentially incubated in biotinylated anti-mouse IgG (1 hr), 0.3% $H_2O_2$ in methanol (20 min), and avidin-peroxidase complex (1 hr), with PBS washings between each step. The slides were incubated in 0.1M Tris-phosphate buffer (pH 7.5) containing 0.005% $H_2O_2$ and 0.5 mg/ml 3,3'-diaminobenzidine until the positive control slide showed evidence of reaction. After washing, the slides were counterstained with methyl-green or hematoxilline.

For western immunoblotting, the following procedure was performed. Tissue samples were homogenized with a Potter in ice-cold 0.1 M Tris-HCl buffer containing 0.1M NaCl and 0.1% aprotinin. $NP_4O$ was added to 0.5% and incubated for 15 min. The lysate was centrifuged for 10 min at 10,000× g. Washed cells were lysed directly in the $NP_4O$ solution then centrifuged for 15 min at 1500× g. The supernatants were incubated at 95° C. for 5 min in 0.025M Tris-HCl buffer containing 0.1% $NaDodSO_4$ and 20% glycerol then loaded onto 10% $NaDodSO_4$/polyacrylamide gels and separated according to the method of Laemmli (Laemmli, U. K., Nature (London) 227:680–685 (1970)). The protein was electrophoretically transferred overnight onto nitrocellulose sheets at 50V in 0.025M Tris buffer containing 0.192M glycine and 20% methanol. The nitrocellulose sheets were incubated 1 hr in Tris-HCl buffered saline (TBS) containing 1% bovine serum albumin, 1% polyvinylpyrrolidone, and 1% non-fat milk, then incubated another 2–3 hrs in the same solution with 1:100 of antibody ascites fluid and 0.05% Tween 20 added. The sheets were washed with TBS and incubated with $10^6$ cpm/ml of $^{125}[I]$-labeled sheep anti-mouse IgF(ab')$_2$ for 2 hrs. The sheets were washed and autoradiographs made.

In total, the above procedure resulted in the isolation of 140 clones capable of secreting antibodies against antigens present on FOCUS cells using the above described indirect binding assay. Among these clones were found the five HCC-selective antibody producing clones of the present invention (designated AF-20, SF-31, SF-90, XF-4 and XF-8), and one normal liver-selective antibody (designated SF-58).

These six antibodies demonstrate that human hepatic transformation is accompanied by significant and measurable antigenic changes. Furthermore, alterations in the hepatocyte antigenic composition are predictable and found consistently in all paired comparisons of transformed and adjacent non-transformed tissue studied to date. Such uniformity in antigenic change emphasizes that there is a strong association of these antigens with the cellular transformation process. Further characterization of these antigens and attempts to identify others will permit a definition of cell surface changes associated with the malignant phenotype.

EXAMPLE 2

Western Blot Analysis

Antigenic extracts were prepared from cultured cell lines and from human tissues as follows. Normal human tissue were obtained from a cadaver within 6 hours after death. Human tumor tissues were obtained from surgical specimens, snap-frozen and kept at −80° C. until use. Confluent cells were harvested from culture flasks using EDTA/versene buffer without proteolytic enzymes, washed twice in PBS and suspended in ice-cold 0.1M Tris-HCl buffer pH 8 containing 0.5% NP40, 0.1M NaCl, and 0.1% aprotinin. After 10 minutes incubation on ice, lysates were centrifuged for 15 minutes at 1500 g at 4° C. Supernatant was harvested, adjusted to a protein concentration of 1 mg/ml, and stored frozen at −80° C. until use. Tissue samples were homogenized using a Potter apparatus in 10 volumes of ice-cold 0.1M Tris-HCl buffer pH 8 containing 0.1M NaCl and 0.1% aprotinin. NP 40 (0.5%) was then added and samples were incubated on ice for 15 minutes and centrifuged at 10,000 g for 10 minutes at 4° C. Supernatant was harvested, adjusted to a protein concentration of 1 mg/ml, and stored at −80° C. until use. For SDS-polyacrylamide gel electrophoresis (SDS-PAGE), the protein preparations were incubated for 5 minutes at 90° C. in a SDS-PAGE buffer and 50 μg of protein was loaded at the top of a 10% SDS polyacrylamide gel and separated according to Laemmli (12). The proteins were electrophoretically transferred onto nitrocellulose paper. The paper was then incubated with 1:100 dilution of ascites fluid (containing antibody) and subsequently with $^{125}[I]$-labeled sheep anti-mouse immunoglobulin F(ab)$_2$ and was exposed for autoradiography.

Western immunoblots demonstrated that SF-31 and SF-90 recognize the same 40 kDa and 50 kDa protein antigens, thus confirming the binding study evidence which suggested these two antibodies recognize the same or closely related epitopes. AF-20 was found to recognize an antigen or approximately 180 kDa. The middle antigen is highly glycosylated as shown by the $^3$H-glucosamine and tunicamycin experiments. These experiments were performed in the following manner:

Tunicamycin treatment of cell lines. Preliminary experiments suggested that maximal inhibition of N-glycosylation with minimal inhibition of protein synthesis occurred using 5 μg/ml tunicamycin. Subconfluent FOCUS cells were starved overnight in methionine-free culture medium containing 10% dialyzed fetal calf serum. The cells were incubated for 1 hr with 5 μg/ml tunicamycin (Sigma), and subsequently then metabolically pulse-labeled by incubating for 1 hr with 20 μCi/ml $^{35}$S-methionine (Amersham, specific activity Ci/mmol). Cells were then harvested, washed twice with PBS, and stored at −80° C.

$^3$H-glucosamine labeling. Confluent cells were incubated with 500 μCi $^3$H-glucosamine (Amersham, specific activity Ci/mmol) for 18 hrs at 37° C. The cells were then harvested, washed twice with PBS, and stored at −80° C.

$^{125}[I]$-cell surface labelings. 1–3×10$^7$ cells were recovered from monolayer culture dishes by incubating for 5–10 min in an EDTA/versene buffer without proteolytic enzymes. The cell suspension was labeled with 1 mCiNa$^{125}$I in the presence of 40 μg lactoperoxidase (Sigma) as described (Carlson, R. L, et al. J. Clin. Invest. 76:40–51 (1985)).

Immunoprecipitation. Solid-phase supports were prepared by covalently binding monoclonal antibodies to protein A Sepharose beads (Schneider, C., et al., J. Biol. Chem. 257:10766–10773 (1982)i Moingeon, P., et al., J. Immunol. 134:2930–2937 (1985)). Cell lysates were pre-cleared by incubating for 1 hr at 4° C. with formalin-fixed Staphylococcus A cells. Additional clearing was performed for 2 hrs at 4° C. by using beads coated with an irrelevant IgG monoclonal antibody. Immunoprecipitation was carried out by incubating the cleaned cell lysate with monoclonal antibody-coated beads for 24 hrs at 4° C.

Furthermore, the AF-20 antigen appears to exist on the cell surface as demonstrated by $^{125}[I]$-labeled protein immunoprecipitation studies. Glycosylation patterns, competitive inhibition experiments, and specificities of binding have shown the SF-25 and AF-20 antigens to be unrelated. The antigens recognized by the XF-4, XF-8, and SF-58 monoclonal antibodies are not detectable by immunoblotting and have yet to be identified and characterized with respect to their molecular weight.

EXAMPLE 3

Comparisons of the Binding of Antibodies to the AF-20, SF-25, SF-31, SF-90, XF-4, XF-8, and SF-58 Antigens An investigation of the binding of the AF-20, SF-25, SF-31, SF-90, XF-4, XF-8, and SF-58 specific antibodies on several HCC and normal liver samples was performed in an attempt to determine whether hepatic transformation was associated with significant antigenic changes. In this study, an attempt was made to control for variation in antigen expression between individuals or to quantitate the antigenic changes observed. In particular, use of malignant and non-transformed liver tissue from individual patients was employed in an attempt to minimize non-antigenic influences on binding activity and thus emphasize those antigenic variations which may be indicative of intrinsic cellular changes. Furthermore, each HCC/non-transformed liver set was assayed against all seven antibodies reported here, thus allowing a demonstration that a given pattern of antigen changes found in one HCC/non-transformed liver set may be stereotypically found in other HCC/non-transformed liver tissues.

The signal-to-noise ratios for indirect binding of these antibodies to six HCC-derived cell lines, to the Veto cell line and to normal peripheral white blood cells (WBC) are shown in FIGS. 1A, 1B, 1C, 1D, 1E and 1F. Four antibodies (AF-20, SF-25, SF-31, and SF-90) bind well to all six HCC cell lines, while XF-4 binds to four out of six and XF-8 binds to four out of five (the sixth HCC cell line was not tested). In contrast to these high rates of binding to HCC cell lines, SF-58 binds to only two of the six HCC cell lines. Antibodies SF-31 and SF-90 bind weakly to Vero and insignificantly to white blood cells (S/N<2.5). None of the other antibodies bind to either Vero or white blood cells. Thus, with the exception of SF-58, these antibodies bind most or all of the HCC cell lines with minimal or no binding to two non-malignant cell types.

Figure 2:
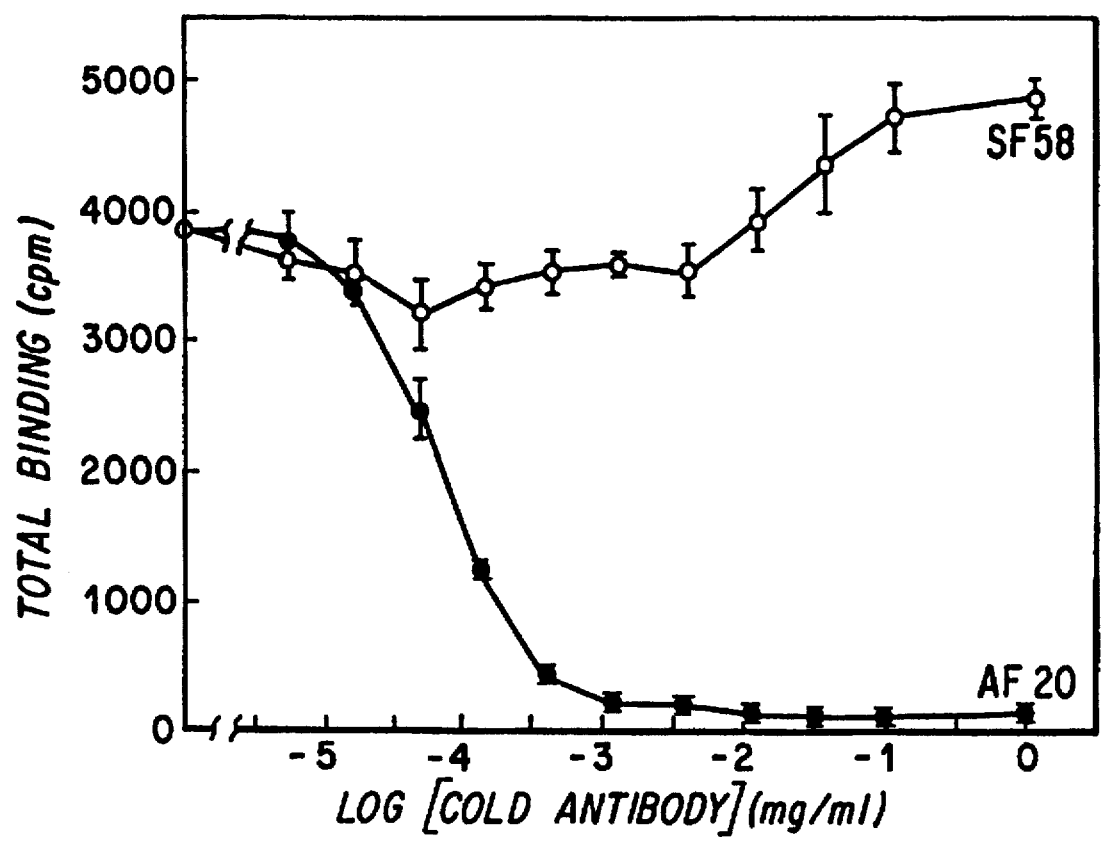
FIG. 2 shows the competitive inhibition of radiolabeled AF-20 using serial dilutions of unlabeled AF-20 and demonstrates that binding is specific with maximal inhibition achieved at an unlabeled AF-20 concentration of 1 mg/ml, and half-maximal inhibition at 0.1 µg/ml. In contrast, SF-58 does not inhibit AF-20 binding at any concentration suggesting that AF-20 and SF-58 recognize separate and distinct epitopes.

Competitive inhibition of radiolabeled antibody binding using unlabeled antibody for blocking demonstrates that for all seven antibodies, greater than 90% of the observed binding is specific and can be inhibited. An example of this competitive inhibition for AF-20 is shown in FIG. 2. Other competitive inhibition studies have demonstrated that SF-31 and SF-90 can completely inhibit each other's binding, suggesting that these two antibodies may recognize the same or adjacent epitopes. The remaining five antibodies are unable to be blocked by any other antibody suggesting that thus each appears to define a distinct and separate membrane-associated epitope.

EXAMPLE 4

Binding of Antibodies to Membrane Preparations

Figure 3:
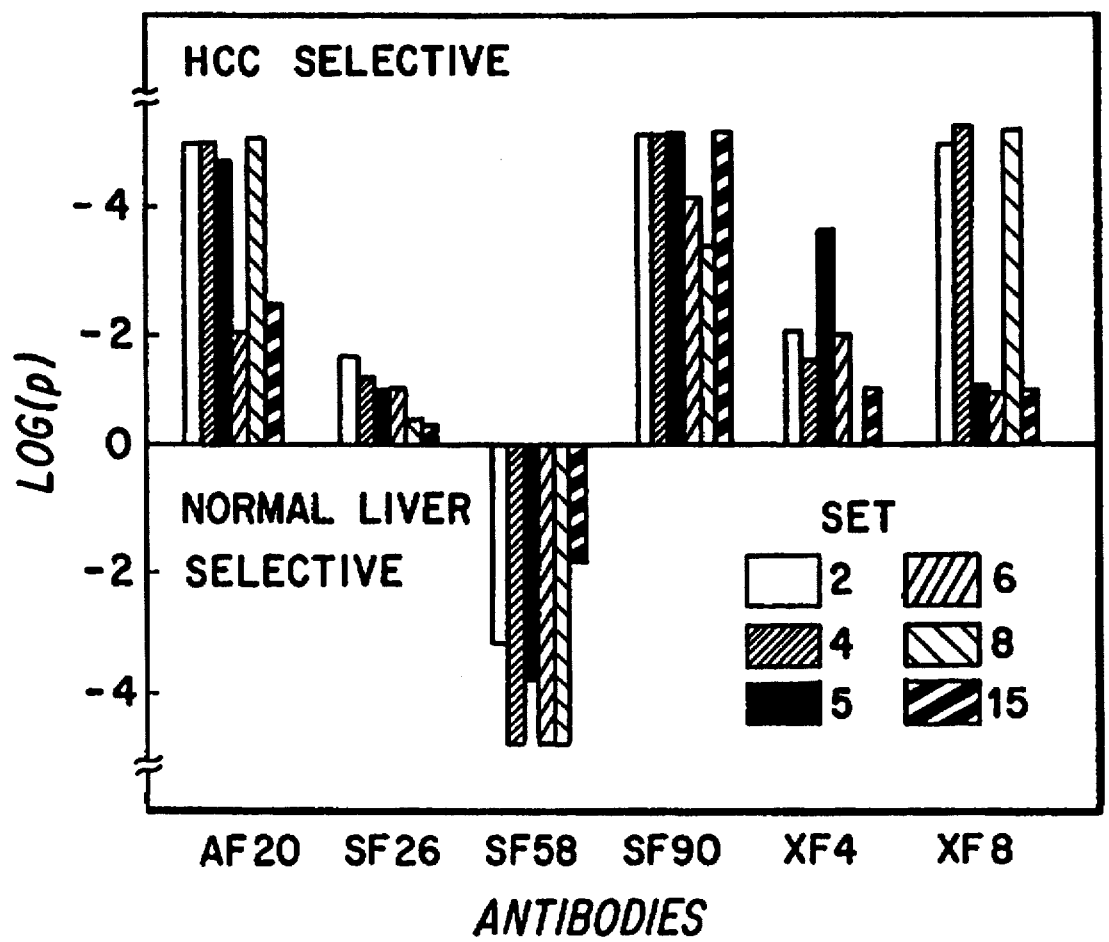
FIG. 3 shows differences in the radiolabeled monoclonal antibody binding with HCC compared to binding with adjacent uninvolved liver. Statistically significant differences in binding are found with a p >0.05. SF-31 was omitted from this figure since its binding activity is identical to that of SF-90 (*: not tested).
Figure 4:
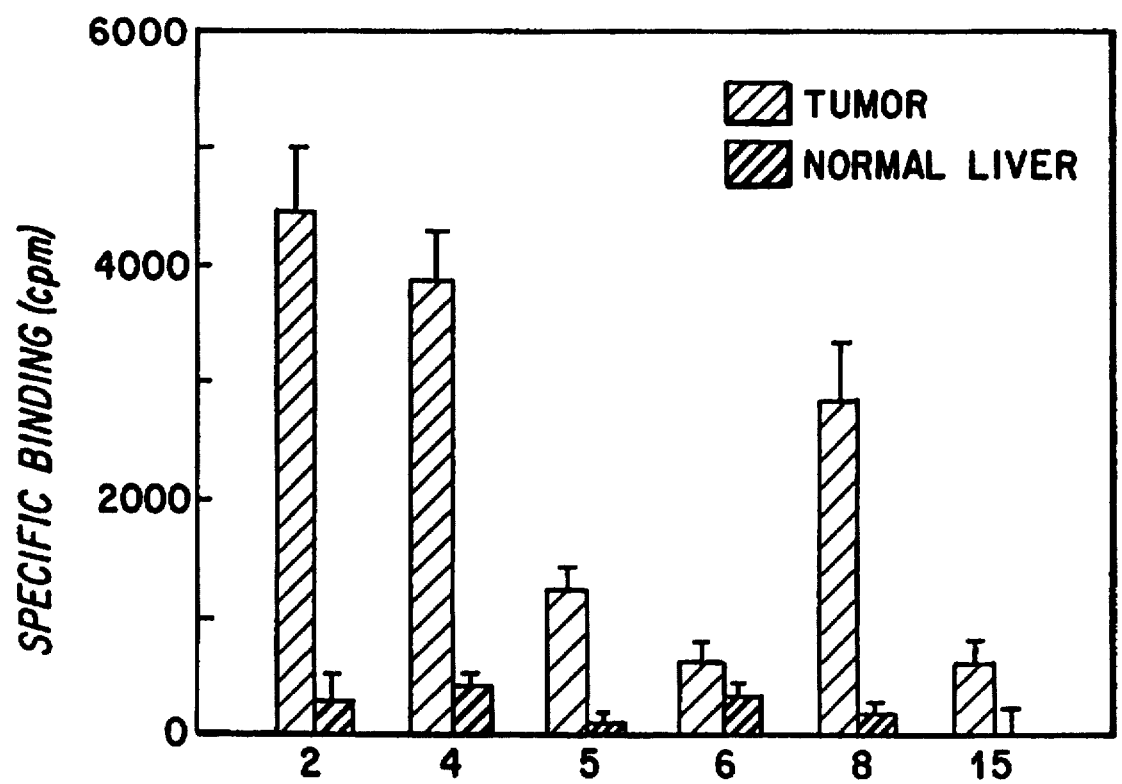
FIG. 4 shows direct radiolabeled AF-20 binding to paired hepatoma and adjacent uninvolved liver sets. For each patient, there is a marked increase in antigen expression on malignant tissue when compared to non-transformed liver tissue. Specific binding was determined by subtracting non-specific binding from total binding.

An immunoassay was developed to measure radiolabeled monoclonal antibody binding to membrane preparations derived from hepatoma tissue and adjacent uninvolved liver from six patients. Protein concentrations were standardized and specific binding was determined by subtracting the non-specific binding (i.e., residual binding in the presence of excess inhibiting cold antibody) from the total binding (i.e., binding in the presence of excess non-inhibiting cold antibody). FIG. 3 is a summary of the antibodies binding to all six HCC/non-transformed liver sets. Antibodies to AF-20, SF-31, SF-90, XF-4, and XF-8 show a striking preference for binding to HCC with significant increases in antigen expression on HCC tissue compared to adjacent non-transformed liver tissue. FIG. 4 presents the actual data for binding of AF-20 to the six pairs of tissue. It shows that there is a high level of antigen expression on the transformed tissue. In contrast, SF-58 shows an entirely different binding pattern with a strong preference for an epitope found on normal liver tissue. With this antigenic determinant, malignant transformation is consistently associated with a decrease in expression.

The SF-25 antigen was found to be too labile to adequately demonstrate its HCC selectivity by the above-described method. Thus, this antigen was studied using the following immunoperoxidase staining method. Immunoperoxidase studies on up to 14 paired HCC/non-transformed liver sets confirmed and expanded on the membrane binding assays by demonstrating significant staining of HCC tissue with no staining of adjacent non-transformed liver for all the antibodies except SF-58. Representative staining patterns for a few of these antibodies were characterized by uniform cellular staining suggesting that most transformed cells, including those which are metastatic, express these antigens. Antibody SF-58 was not found to stain HCC. The SF-31, SF-90, XF-4, and XF-8 antigens were stable after formaldehyde fixation and paraffin embedding. In contrast, the SF-25 and AF-20 antigens are only identifiable in fresh frozen sections of HCC suggesting that these antigens are labile.

Indeed, these seven antibodies demonstrate a consistent pattern of antigen alteration. Six antibodies (AF-20, SF-25, SF-31, SF-90, XF-4, and XF-8) recognize antigens which are present on HCC cell lines and on HCC tissues in vivo but are only weakly, if at all, expressed on the adjacent non-transformed liver. Immunoperoxidase staining demonstrated that these antigens are expressed on most, if not all, cells within a given HCC tumor. The strong association between malignant transformation and the constitutive expression of these antigens suggests that they may play an important role on the surface of hepatoma cells. In contrast, SF-58 recognizes an antigen which shows consistent decreases in expression on the transformed tissue with high levels of expression on normal liver tissue.

Studies showing antibody binding to live cells demonstrated that these antibodies recognize cell surface epitope. SF-31 and SF-90 recognize the same two 40 kDa and 50 kDa proteins and can competitively inhibit each other's binding. AF-20 recognized an antigen of approximately 180 kDa while SF-25 recognized a 120 kDa protein (Wilson et al., supra). The AF-20 and SF-25 antigens are labile and subject to inactivation by mild fixation, denaturation, and detergents. The SF-58, XF-4, and XF-8 antigens have not yet been molecularly characterized.

EXAMPLE 5

XF-8 Specific Antibody Detects an Antigen Common to Human Colon, Liver and Lung Adenocarcinoma The monoclonal antibody (MAb) XF-8 was produced as follows. The hepatocellular carcinoma cell line, FOCUS, was used for immunization of mice. An early passage of this cell line from the original tumor had been kept in liquid nitrogen. It was subsequently regrown and harvested from monolayer culture. Primary immunizations were accomplished with 4.0×10⁶ cells/ml in 50% complete Freund's adjuvant using intact whole cells and were injected intraperitoneally into female Balb/c mice. After 6 to 10 weeks, the secondary immunizations were performed by an intravenous inoculation of 4.0×10⁶ cell in 200 µl PBS. Splenocytes were fused with the parent myeloma cell line (X63) 3 days after. The resulting hybridomas were selectively maintained in HAT medium, then cloned by limiting dilution.

One of MAbs, XF-8 was tested for reactivity to human adenocarcinoma of the colon, lung and liver as well as adjacent normal counterpart and other normal tissues by radioimmunohistology. Adenocarcinoma of the colon, lung and liver as well as adjacent normal counterparts and other normal tissues were obtained from fresh surgical specimens or as rapidly as possible from autopsies. These tissues were immediately embedded in OCT compound (Miles Scientific, Naperville, Ill.) and frozen in liquid nitrogen and stored at −80° C. Tissue sections cut from these snap-frozen tissues were dried onto glass slides and fixed in cold acetone for 5 minutes. These section were then incubated with $^{125}$I-labeled SF-25 (10⁶ cpm/100 µl) in 20 mM PBS, pH 7.2 containing 20% calf serum at 4° C. for overnight. After washing in 20 mM PBS, pH 7.2 for 60 minutes with three changes, the sections were fixed in 10% formalin solution in saline for 10 minutes. After 10 minutes wash in PBS tissues were stained with eosin (1% eosin Y in 100% ethanol) for 5 minutes and destained with 100% ethanol and dried. These sections were then dipped for 2 seconds in autoradiographic emulsion (Kodak autoradiography emulsion type NTB 3: Eastman Kodak Co., Rochester, N.Y.) diluted 1:1 with distilled water and maintained at 45° C. in a water bath. The slides were dried for 60 minutes in the air and placed in light-tight wooden boxes (Fischer Scientific Co., Pittsburg, Pa.). After 6 to 12 hours exposure at 4° C. the slides were developed in Kodak Dektol, D19 (Eastman Kodak Co., Rochester, N.Y.) for 90 seconds, dipped in Liquid Hardener (Eastman Kodak Co., Rochester, N.Y.) for 15 seconds to stop reaction and fixed in Rapid Fix (Eastman Kodak Co., Rochester, N.Y.) for 3 minutes. After washing sections in Hypo Clearing Agent (Eastman Kodak Co., Rochester, N.Y.) for 2 minutes and in distilled water for 5 minutes, they were air-dried and counterstained with Gill's #3 hematoxylin (Fischer Scientific Co., Pittsburg, Pa.). These tissue section were then exposed against Kodak X-ray film XOMAT-AR (Eastman Kodak Co., Rochester, N.Y.) to perform semi-quantitative and comparative analysis of the XF-8 antigen expression in adenocarcinomas and normal tissues by macroscopic autoradiography.

Figures 6A, 6B:
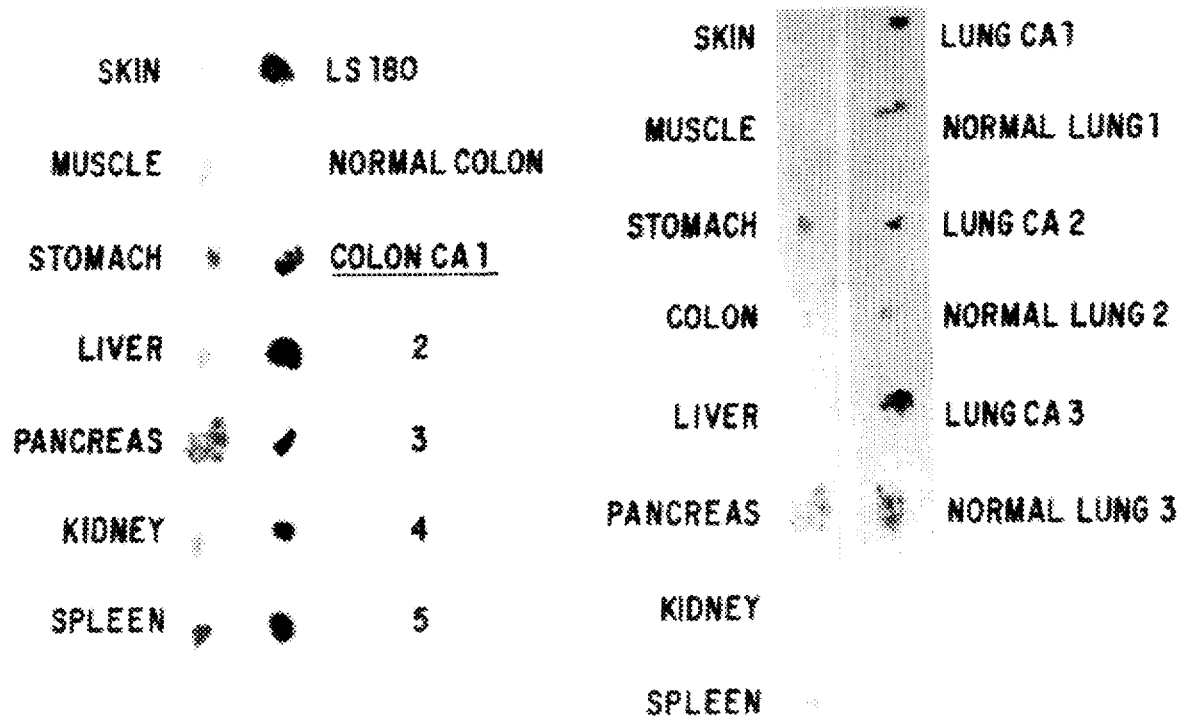
FIGS. 6A and 6B are autoradiographs which demonstrate the expression of XF-8 antigen in vivo on fresh tissues.

FIG. 5 is an autoradiography that demonstrates expression of XF-8 antigen on hepatoma tissues, adjacent non-tumor livers and other normal tissues. The antigen is highly expressed on the FOCUS hepatoma cell line used as the immunogen and is also highly expressed on fresh human hepatoma tissues. The antigen is not expressed on non-tumor tissue of liver nor other normal human tissues. Similarly, as shown in FIGS. 6A and 6B, the XF-8 antigen is highly expressed in vivo on fresh tissue of human colon and lung adenocarcinoma. In fact, 17/17 hepatocellular carcinoma, 15/15 colon adenocarcinoma and 5/5 lung adenocarcinoma expressed this antigen. The XF-8 antigen appears to be shared by a variety of human adenocarcinomas and is present on the cell surface of human adenocarcinoma as a novel common antigenic determinant.

Further evidence for in vivo expression of such an antigen was determined by tumor targeting experiments using $^{125}$I-labeled XF-8 MAb. As shown in Table 3, the biodistribution of XF-8 in nude mice bearing a human hepatocellular carcinoma demonstrates the specific uptake of XF-8 MAb in tumor. In this experiment, the mice were given simultaneous injections of 10 µCi of $^{125}$I-labeled specific antibody of interest (XF-8) and 1 µCiu of $^{131}$I-labeled non-specific antibody termed B2TT. The mice were sacrificed and dissected at 24, 48 and 72 hours after injection. Tumor, blood, thyroid, heart, lung, kidney, stomach, intestine, liver and spleen were weighed on an analytical balance assayed for radioactivity using a multichannel, well-type gamma counter (a window from 15 to 50 KeV for $^{125}$I and a window from 50 to 330 KeV for $^{131}$I). The result was expressed as localization index, i.e., the ratio of specific $^{125}$I to nonspecific $^{131}$I activity in tumor and in tissues divided by the same ratio in the blood. Table 3 shows the localization index of XF-8 at 72 hours after injection of radiolabeled antibodies. Localization index in hepatoma tissue was 2.72±1.25, demonstrating the specific uptake of XF-8 in tumor compared with normal tissues (localization index 0.93–1.46) (P<0.001).

Figure 7A:
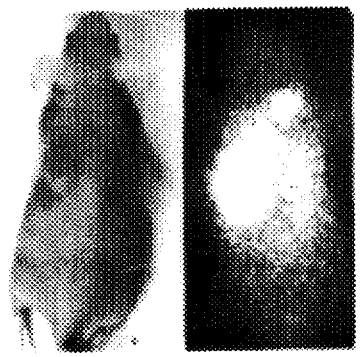
FIGS. 7A, 7B and 7C shows the nuclear imaging of hepatocellular carcinoma in a nude mouse model with XF-8 and AF-20 antigen reacting monoclonal antibodies.
Figure 7B:
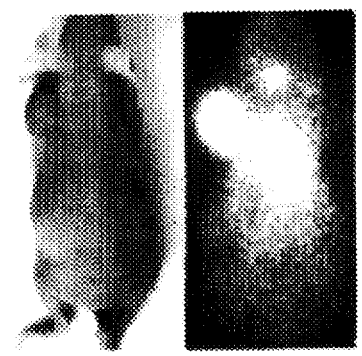
Figure 7C:
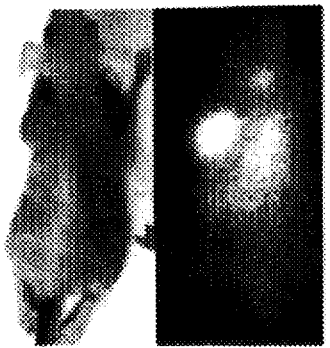

These results demonstrates that the XF-8 antibody may be used as an immunotargeting agent in vivo and could be employed for imaging and immunotherapy of adenocarcinoma in man. Indeed, when nuclear imaging of hepatocellular carcinoma was performed using a nude mouse model, it was possible to clearly identify this tumor (FIGS. 7A, 7B and 7C). The nuclear imaging study was performed by injecting 150 to 250 µCi of $^{125}$I-labeled intact whole antibodies i.v. via tail vein into each mouse bearing tumor. Images were obtained at 6, 24, 48, 74 and 120 hours. The mice were anesthetized and images were obtained in posterior views using a scintillation camera interfaced to a computer. No background subtraction nor computer smoothing was employed. This figure shows a representative imaging study demonstrating the specific localization of tumors at 72 hours.

EXAMPLE 6

AF-20 Specific Antibody Detects an Antigen Common to Human Colon, Lung and Liver Adenocarcinoma The MAb AF-20 was produced according to the same protocol as MAb XF-8 except that the NS1 myeloma cell line was used for cell fusion.

MAb AF-20 was tested for reactivity to human adenocarcinoma to examine the in vivo expression of this antigen. Adenocarcinoma of the colon, lung and liver as well as adjacent normal counterparts obtained from fresh surgical specimens and other normal tissues obtained as rapidly as possible from autopsies were used for this study. The radioimmunohistology technique was performed as described above.

FIG. 8 is an autoradiography on X-ray film that demonstrates the expression of AF-20 antigen on hepatoma tissues compared with adjacent non-tumor parts of liver and other normal tissues. The antigen is highly expressed on the FOCUS hepatoma cell line used as the immunogen. This antigen is also highly expressed on fresh human hepatoma tissues. Note that the hepatoma tissue section indicated as "Hepatoma 1" in FIG. 8 is the tumor from which the FOCUS cell line was established. In contrast, AF-20 antigen is not expressed on non-tumor liver tissues. This antigen is expressed on the human adrenal cortex but it is not expressed on other normal human tissues (FIG. 8). Similarly, as shown in FIG. 9A, and 9B, the SF-20 antigen is highly expressed in vivo on fresh tissue of human colon and lung adenocarcinoma (antigen was positive in 17/17 hepatocellular carcinoma, 20/20 colon adenocarcinoma and 5/5 lung adenocarcinoma). The expression of AF-20 antigen in adenocarcinoma of liver, colon and lung in vivo are representative examples to demonstrate that the AF-20 antigen is shared by a variety of human adenocarcinomas and is present on the cell surface as a novel common antigenic determinant.

Further evidence for in vivo expression of such an antigen was determined by tumor targeting experiment using $^{125}$I-labeled AF-20 MAb. The biodistribution of $^{125}$I-labeled AF-20 MAb injected into nude mice bearing a human hepatocellular carcinoma was examined. In this experiment, the mice were given simultaneous injections of 10 µCi of $^{125}$I-labeled specific antibody of interest (AF-20) and 1 µCi of $^{131}$I-labeled non-specific antibody (B2TT). The mice were sacrificed and radioactivity of each tissue was counted as described before. The biodistribution of AF-20 is demonstrated by a localization index in Table 2. Localization index of AF-20 at 72 hours in hepatoma tissue was found to be 2.82±1.16, demonstrating a specific increased uptake of MAb AF-20 in tumor compared with normal tissues (localization index 1.09–1.79) (P<0.001).

These results demonstrate that AF-20 antibody may be used as an immunotargeting agent in vivo as well as XF-8. Radiolabeled AF-20 was also tested for imaging of hepatocellular carcinoma in the nude mouse model. As shown in FIGS. 7A, 7B and 7C, it was possible to demonstrate the localization of tumor using $^{125}$I-labeled AF-20 MAb. A combination of XF-8 and AF-20 MAbs labeled with $^{125}$I as imaging agents is also shown in FIGS. 7A, 7B and 7C. These images indicate that the use of both antibodies may be employed to enhance tumor visualization.

TABLE 2

Biodistribution of MAbs XF-8 and AF-20 in Nude Mice Bearing Human Hepatocellular Carcinoma Xenografts

| Tissue | Localization Index* | |
|---|---|---|
| | XF-8 | AF-20 |
| Blood | 1.00 ± 0.00 | 1.00 ± 0.00 |
| Intestine | 1.07 ± 0.07 | 1.09 ± 0.02 |
| Stomach | 1.21 ± 0.07 | 1.26 ± 0.05 |
| Liver | 0.93 ± 0.13 | 1.16 ± 0.11 |
| Spleen | 1.40 ± 0.20 | 1.48 ± 0.11 |
| Kidney | 1.07 ± 0.05 | 1.09 ± 0.04 |
| Heart | 1.46 ± 0.18 | 1.28 ± 0.13 |
| Lung | 1.17 ± 0.05 | 1.11 ± 0.03 |
| Neck | 1.35 ± 0.66 | 1.79 ± 0.36 |
| Tumor | 2.72 ± 1.25 | 2.82 ± 1.16 |

*Localization index is the ratio of specific $^{125}$I to nonspecific $^{131}$I activity in tumor and in tissues divided by the same ratio in the blood. The results are expressed as mean ± S.D. of three experiments.

EXAMPLE 7

XF-8 and AF-20 Detect Antigens Common to a Variety of Human Adenocarcinoma

Table 3 shows the results of direct binding to a variety of human adenocarcinoma cell lines using $^{125}$I-labeled XF-8 and AF-20. This assay was carried out in 96-well filter-bottomed plates (V & P Scientific Inc., San Diego, Calif.). Plates were first filled with 100 µl of bovine serum for 30 minutes at room temperature, in order to block non-specific protein binding sites. Labeled MAbs adjusted to $10^5$ cpm/100 µl of PBS containing 20% calf serum was incubated with $10^5$ target cells for one hour at room temperature. The cells were then washed three times with PBS and the radioactivity of dried filters were counted by gamma well counter. Results are expressed as signal to noise ratio (S/N ratio), i.e., the ratio of cpm bound to adenocarcinoma cell line divided by cpm bound to monkey kidney cell line (Cos-1 cell) used as a negative control cell line. As shown in Table 3, both MAb XF-8 and MAb AF-20 bind to all the human adenocarcinoma cell lines examined, demonstrating that these MAbs recognize cell surface antigens expressed constitutively on human adenocarcinomas.

TABLE 3

Direct Binding of XF-8 and AF-20 Monoclonal Antibodies to Human Adenocarcinoma Cell Lines

| Cell Lines | Origin | Binding of XF-8 (S/N ratio*) | Binding of AF-20 (S/N ratio*) |
|---|---|---|---|
| FOCUS | Liver | 19.53 ± 0.56 | 30.68 ± 2.15 |
| Hep G2 | Liver | 17.59 ± 1.21 | 22.88 ± 1.83 |
| Hep 3B | Liver | 11.31 ± 0.13 | 11.31 ± 0.51 |
| PLC/PRF/5 | Liver | 7.70 ± 0.20 | 13.22 ± 1.87 |
| MAHLAVU | Liver | 22.09 ± 0.36 | |
| SK-HEP-1 | Liver | 23.17 ± 5.93 | |
| LS 180 | Colon | 10.72 ± 0.70 | 17.40 ± 1.93 |
| Colo 320 | Colon | 4.99 ± 0.31 | 8.72 ± 0.27 |
| HT-29 | Colon | 3.71 ± 3.22 | 3.11 ± 2.70 |
| WiDi | Colon | 2.44 ± 0.28 | |
| SK-CO-i | Colon | 3.16 ± 0.64 | |
| SW403 | Colon | 7.35 ± 0.68 | |
| CaCo 2 | Colon | 8.47 ± 0.44 | |
| A-427 | Lung | 2.46 ± 0.38 | 7.51 ± 2.24 |
| CALU-3 | Lung | 4.79 ± 0.56 | |
| BT-20 | Breast | | 6.86 ± 0.96 |
| A-498 | Kidney | 3.00 ± 0.28 | 8.16 ± 1.44 |
| SW-13 | Adrenal cortex | 31.06 ± 1.39 | 45.54 ± 2.03 |
| Caov-3 | Ovary | 3.05 ± 0.4 | 9.58 ± 1.28 |
| HeLa | Uterus | 5.57 ± 0.14 | 13.08 ± 3.11 |
| AN3 CA | Endometrium | | 6.35 ± 1.80 |
| WBC$^1$ | PBL | 0.61 ± 0.08 | 1.10 ± 0.08 |

*Monkey kidney cell line (Cos-1 cell line) was used as a negative control cell line. Results are expressed as signal to noise ration (S/N ratio), i.e., the ratio of cpm bound to adenocarcinoma cell line divided by cpm bound to Cos-1 cell. Positive result is S/N > 2.0. All cell lines are human origin adenocarcinoma. PBL - Peripheral Blood Lymphocyte.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A monoclonal antibody, or F(ab) or F(ab)$_2$ fragment thereof, which specifically binds to an adenocarcinoma cell antigen AF-20, and which has the epitope binding specificity of an antibody produced by hybridoma cell line ATCC designation HB 9687.

2. A monoclonal antibody, or F(ab) or F(ab)$_2$ fragment thereof, which specifically binds to an adenocarcinoma cell antigen XF-8, and which has the epitope binding specificity of an antibody produced by hybridoma cell line ATCC designation HB 9686.

3. The monoclonal antibody (MAb) of claim 1, wherein said MAb is a murine MAb.

4. The monoclonal antibody (MAb) of claim 2, wherein said MAb is a murine MAb.

5. The monoclonal antibody according to claim 1, which is produced by hybridoma cell line ATCC designation HB 9687.

6. The monoclonal antibody according to claim 2, which is produced by hybridoma cell line ATCC designation HB 9686.

7. A hybridoma cell line which produces the monoclonal antibody of claim 1.

8. A hybridoma cell line which produces the monoclonal antibody of claim 2.

9. A hybridoma cell line (ATCC designation HB 9687) which produces the monoclonal antibody of claim 5.

10. A hybridoma cell line (ATCC designation HB 9686) which produces the monoclonal antibody of claim 6.

* * * * *